(12) United States Patent
Tribble et al.

(10) Patent No.: US 11,250,957 B2
(45) Date of Patent: *Feb. 15, 2022

(54) MEDICATION PREPARATION SYSTEM

(71) Applicant: BAXTER CORPORATION ENGLEWOOD, Englewood, CO (US)

(72) Inventors: Dennis Tribble, Ormond Beach, FL (US); Abdul Wahid Khan, Lindenhurst, IL (US); Dennis Schneider, Nashua, NH (US); Gregory T. Olsen, DeLand, FL (US); Jayson Lee Bender, Ormond Beach, FL (US); Bhavesh S. Padmani, Port Orange, FL (US); Matthew A. Valentine, Ormond Beach, FL (US)

(73) Assignee: Baxter Corporation Englewood, Englewood, CO (US)

( * ) Notice: Subject to any disclaimer, the term of this patent is extended or adjusted under 35 U.S.C. 154(b) by 242 days.

This patent is subject to a terminal disclaimer.

(21) Appl. No.: 16/504,922

(22) Filed: Jul. 8, 2019

(65) Prior Publication Data

US 2019/0333618 A1 Oct. 31, 2019

Related U.S. Application Data

(63) Continuation of application No. 15/699,737, filed on Sep. 8, 2017, now Pat. No. 10,347,374, which is a continuation of application No. 14/022,415, filed on Sep. 10, 2013, now abandoned, which is a
(Continued)

(51) Int. Cl.
*G16H 20/10* (2018.01)
*G16H 70/40* (2018.01)
*G06Q 10/08* (2012.01)
*G16H 40/63* (2018.01)
*G16H 40/67* (2018.01)
*G16Z 99/00* (2019.01)
*G16H 20/17* (2018.01)
*G16H 10/60* (2018.01)
*G16H 20/13* (2018.01)

(52) U.S. Cl.
CPC ............ *G16H 70/40* (2018.01); *G06Q 10/08* (2013.01); *G16H 10/60* (2018.01); *G16H 20/10* (2018.01); *G16H 20/13* (2018.01); *G16H 20/17* (2018.01); *G16H 40/63* (2018.01); *G16H 40/67* (2018.01); *G16Z 99/00* (2019.02)

(58) Field of Classification Search
None
See application file for complete search history.

*Primary Examiner* — Jonathan Ng
(74) *Attorney, Agent, or Firm* — K&L Gates LLP

(57) ABSTRACT

A system for preparing compounded medication doses is disclosed. The system includes a computerized medication compounding workstation configured to receive a batch compounded medication dose order over a network and retrieve an electronically stored protocol having a set of steps to prepare compounded medication doses specified by the batch compounded medication dose order. The example workstation is also configured to display, on a graphical user interface to a pharmacy operator, information related to the set of steps for preparing the compounded medication doses and receive input related to the preparation of the compounded medication doses including at least medication information scanned from at least one source medication container and a digital image from a digital camera. The workstation verifies completion for each step before allowing the pharmacy operator to move to a next step to prepare the compounded medication doses.

20 Claims, 13 Drawing Sheets

Related U.S. Application Data continuation of application No. 12/358,574, filed on Jan. 23, 2009, now Pat. No. 8,554,579.

(60) Provisional application No. 61/104,954, filed on Oct. 13, 2008.

FIG. 8

MEDICATION PREPARATION SYSTEM

PRIORITY

This application claims priority to and the benefit as a continuation application of U.S. patent application Ser. No. 15/699,737, now U.S. Pat. No. 10,347,374, filed Sep. 8, 2017, which claims priority to and the benefit as a continuation application of U.S. patent application Ser. No. 14/022, 415, filed Sep. 10, 2013, which claims priority to and the benefit as a continuation application of U.S. patent application Ser. No. 12/358,574, now U.S. Pat. No. 8,554,579, filed Jan. 23, 2009, which claims priority to and the benefit of U.S. Provisional Patent Application No. 61/104,954, filed Oct. 13, 2008, the entire contents of each of which are hereby incorporated by reference and relied upon.

TECHNICAL FIELD

The present invention relates to the management of medication dose orders and medication dose preparation, and more particularly to some or all of the systems and steps taken in connection with the receipt, processing, filling on-demand and in anticipation of use, management, and distribution of medication dose orders, as well as remote dose inspection for facilitating the practice of telepharmacy.

BACKGROUND

In many medical facilities, medication orders are transmitted to a pharmacy from various locations throughout the hospital and by various means of communication. The process by which these medication orders are managed involves many discrete steps. Orders must be entered, transmitted and received by the pharmacy, validated, and filled according to manufacturer's specifications or established institutional guidelines. The filling process involves the selection and, where required, preparation of drug products for administration to patients in compliance with the validated order. Once filled, the resulting drug products (i.e., doses) must be delivered to the patient that requires them. One environment, by way of example, in which such transmissions and processes occur, is a hospital.

There are points in the process that are susceptible to miscommunication or loss of information. This can be problematic in terms of logging and auditing the processing and preparation of medications, which is often mandated by insurance and regulatory requirements.

The pharmacy operationally receives these medication dose orders in the form of printed labels, typically generated by a hospital pharmacy computer system, one for each medication dose order to be dispensed. In many cases, a separate label is printed for each dose to be dispensed. Pharmacists and technicians use these labels as work documents to identify the medications to make and properly prepare and issue the desired medication. The labels are then used as address labels to ensure that the medications are routed to the correct patient for use. These labels lack detailed preparation steps, causing the technician to rely on his or her memory of the preparation procedures and guidelines, seek input from a co-operator, or find a manufacturer's package insert or a written institutional guideline.

One hazard of this method is that the label represents the only record of the work needing to be performed with the result that, if the label is lost or damaged, the work may not be performed (that is, the medication dose order may not be fulfilled) and the omission does not become known until a caregiver complains because they cannot locate the medication, or because a patient experiences an adverse event because of omitted medication.

U.S. Pat. No. 7,096,212 for "Serial Data Capture and Processing" and U.S. Patent Publication No. 2003/0097368 for "Data Transmission Capture in Support of Medication Preparation" describe technology for automating the preparation of medication dose orders in response to the printing of such labels, the entire disclosures of which are hereby incorporated by reference, as though set forth in their respective entireties. However, these systems do not manage the distribution of medication dose orders to the various pharmacy workstations at which they are to be prepared, nor do they track the distribution of the completed dose orders to the patient for whom they are intended.

While many medications can be prepared by automated systems containing "built in" knowledge of correct preparation procedures, there are still large numbers of medication dose orders that require manual preparation, or institutions whose size precludes the incorporation of automation technology. The information and knowledge regarding how to prepare the medication is typically transferred verbally from one person to another. Thus, if a clinician receives an order for which he is unaware of the correct procedure for fulfillment, the clinician would have to request assistance, and thereby acknowledge a lack of training for that particular task. However, seeking training can be a source of embarrassment or be perceived as an undesired delay, either scenario providing a potential basis for the clinician to potentially use an improper procedure for the preparation of a particular medication, significantly increasing the possibility of a serious medication error due to flawed preparation procedures. Repeated conduct in this regard can result in "self trained" experience in a manner which is inconsistent with published procedures for handling that medication. Typically, the correct procedures are defined and written in a manual or other documentation. However, there is currently no efficient way to present the relevant excerpt of the manual to the clinician in relation to the particular medication order to be processed.

Furthermore, after a doctor or nurse enters a medication order, determining the status of the order requires manual intervention. The progress of the order can not easily be determined. The order must be located, determined if it has been filled, then possibly located somewhere throughout a facility, such as a hospital, which can be complicated further as the medication dose is being transferred to the patient or as patients are moved from one location to another (e.g., from the patient's room to physical therapy or a lab).

Workload management systems for hospitals and sterile products preparation are unsophisticated and incapable of properly managing the process, causing conflicts between the level of staffing provided and the level of work to be performed.

Centralized preparation of medication dose orders within a hospital or pharmacy creates a further set of logistical problems. A large number of medication dose received within the same general time frame can quickly outpace the production capabilities of the hospital. Further, hospital pharmacies generally have no way of separating medication dose orders that are needed immediately from those dose orders that are less urgent.

For example, IV rooms currently operate via manual distribution of labels and this type of system can lead to a number of problems, including the following problems. Currently, a pharmacy that "kits" work for transmission to the IV room obtains one or more labels from a label printer, mentally determines what products and supplies are needed to prepare the requested doses, assembles those items, places the items and the labels in a bin and passes that bin into the IV room. There is no verification of correct drugs. In addition, doses are not tracked; doses become acknowledged as "lost" when a nurse indicates that an expected dose was not received at the patient care area. Some doses are very difficult to track because they cannot be prepared as soon as the label is received. Manual tracking methods often result in those doses being overlooked. There are currently no tracking metrics can definitively state what amount of work is to be done, or where the IV room is in the completion of that work.

In addition, a pharmacist by law has to approve each drug order before it can be released and delivered to a patient. Since this is a state regulated activity, there are a number of different rules and regulations imposed by the state on pharmacists in terms of the level of supervision required by a pharmacist in monitoring and approving drugs prepared by others. For example, a pharmacist may be able to approve a drug order and release it even if the pharmacist is in a different room of the same building; however, it is clear, that the pharmacist cannot approve a drug order from a remote location outside the building, such as, the home of the pharmacist or some other location. These rules and regulations can potentially limit the efficiency of the pharmacy since an order can not be released until approved by a pharmacist and therefore, if the pharmacist is temporarily unavailable, etc., the order will be delayed.

The present disclosure addresses one or more of these and other problems to provide a centralized medication order management, fulfillment, and tracking system. As more and more automated dispensing devices are developed, there is additional value in a mechanism in accordance with the present disclosure for automatically routing medication dose orders generated by the hospital pharmacy computer system to the most appropriate automated or manual workstations in the pharmacy and then tracking them to ensure that they are completed and distributed to their intended recipients.

SUMMARY

One aspect of the present disclosure concerns a method for performing telepharmacy in which a dose order is received and processed at a machine executing code that forwards the processed dose order to a medication preparation station. The dose is prepared at the medication preparation station, based on the dose order, and the preparation includes following a recipe provided by the machine to the medication preparation station. Information that relates to actions taken to follow the recipe are captured and then stored at a database. The captured information is accessed from a remote site using a portal in communication with the database. The prepared does is inspected through the portal, and the captured information is reviewed in order to verify whether the dose has been prepared in accordance with the recipe. If the reviewer confirms that that the dose has been prepared in accordance with the recipe, then he or she approves the release of the dose to the patient.

In another aspect of the present disclosure, a centralized system for preparing and managing patient-specific dose orders entered into a system comprises an order processing server, a dose preparation station, and a display. The order processing server executes software on a processor thereof and is connected by a network to the first system. The order processing server is configured to receive the patient-specific dose orders from the first system and includes a database configured to store the dose orders and information that relates to the dose orders. The order processing server is further configured to generate a dose order queue listing all dose orders received by the order processing server. The dose preparation station is adapted for the preparation of a plurality of doses based on received dose orders. The dose preparation station is in bi-directional communication with the order processing server and has an interface for providing an operator with a protocol associated with each received drug order and specifying a set of steps to fill the drug order. The dose preparation station is further configured to present the protocol and has one or more data input devices to capture information that relates to the set of steps to fill the drug order. The display is communicatively coupled to the order processing server to output the dose order queue and metrics concerning activity at the dose preparation station. The display is positionable independently of the dose preparation station.

In a further aspect of the present disclosure, a system for preparing patient-specific drug doses includes a dose preparation station having a work area adapted for the preparation of a plurality of drug doses corresponding to at least a portion of patient-specific dose orders that originate from another system. An interface at the station has a display and one or more input devices. A computer associated with the station executes code that is operative to receive a protocol associated with the preparation of each of the drug doses, to display the protocol for a given one of the drug doses, and to capture information that relates to completion of steps defined by the protocol to prepare that drug dose using the one or more input devices.

In still a further aspect of the disclosure, a system is provided that is configured, among other things, to provide drug order preparation benchmarks to an administrator. Such a system cooperates with a plurality of local servers each associated with a hospital or pharmacy and comprises a central server, a dose metrics module, and an output module. The central server has a selective communication link to the plurality of local servers and is configured to receive drug order preparation data from each local server. The dose metrics module has access to the drug order preparation data and is operative to process the drug order preparation data of at least one local server in accordance with a rule so as to output a performance metric. The output module is operative to compare the performance metric of the at least one local server to the performance metric associated with one or more of the plurality of local servers.

The system as described in the foregoing paragraphs optionally can have a database connected so as to maintain the data received from each local server, such as drug order preparation data. A tabulation module can be operative to process such data from each local server and to generate billing data as a function of said processing. The processing can comprise a tally of records uploaded to the central server by each local server. A communications module can be operative to forward the billing data to a prescribed destination, including to one of the local servers. The billing data can be forwarded by the communications module in the form of an invoice.

In yet another aspect of the disclosure, a system for preparing patient-specific drug doses based upon drug orders that have been entered into a first system comprises an order processing server, a plurality of dose-preparation stations, and a display. The order processing server of such a system executes software on a processor thereof and is connected by a network to the first system and configured to receive the patient-specific dose orders from the first system. In addition, the order processing server includes a database configured to store the dose orders and information that relates to the dose orders and is further configured to generate a dose order queue listing all dose orders received by the order processing server and has a first mode of operation in which drug orders are parsed and sent to a select dose preparation station based on at least one optimization criteria and a second mode of operation in which individual drug preparation stations select drug orders to fulfill at which time the drug order is assigned to the drug preparation station. The dose-preparation stations are for preparing a plurality of doses based on received dose orders. Each dose preparation station is in bi-directional communication with the order processing server and has an interface for providing an operator with information relating to drug preparation and also to allow the operator to input information in furtherance of a protocol having a drug-identification integrity-check process. The display is communicatively coupled to the order processing server and is positionable independent of the dose preparation station. The display outputs the dose order queue and metrics concerning activity at each dose preparation station. Dose labels for placement of completed drug orders are only printed at the dose preparation station that was responsible for preparation of the drug. These and other aspects, features and advantages of the present disclosure can be appreciated further from the description of certain embodiments and the accompanying drawing figures.

BRIEF DESCRIPTION OF THE FIGURES

FIG. 8 is an exemplary display of a dose verification screen for verifying that the prepared dose is the proper, intended dose of medication.

DETAILED DESCRIPTION

The present disclosure relates to the capture, processing, tracking, approval and distribution of medications. More particularly, the disclosure relates to an at least partially automated fulfillment system and method for receiving incoming medication dose orders, and processing those orders, preferably in an efficient and optimized manner, through the selective use of either an automated medication preparation fulfillment system or a manual medication preparation system. Optionally, each prepared medication dose can be tracked through to its predetermined destination. In addition, the present disclosure relates to a system and process by which individual processing steps that are taken in preparing a dose of medication are captured and stored for later verification that the dose was properly prepared. In addition, the present disclosure relates to software-based systems that operate to provide a portal for dose inspection that facilitates the practice of telepharmacy.

Figure 3:
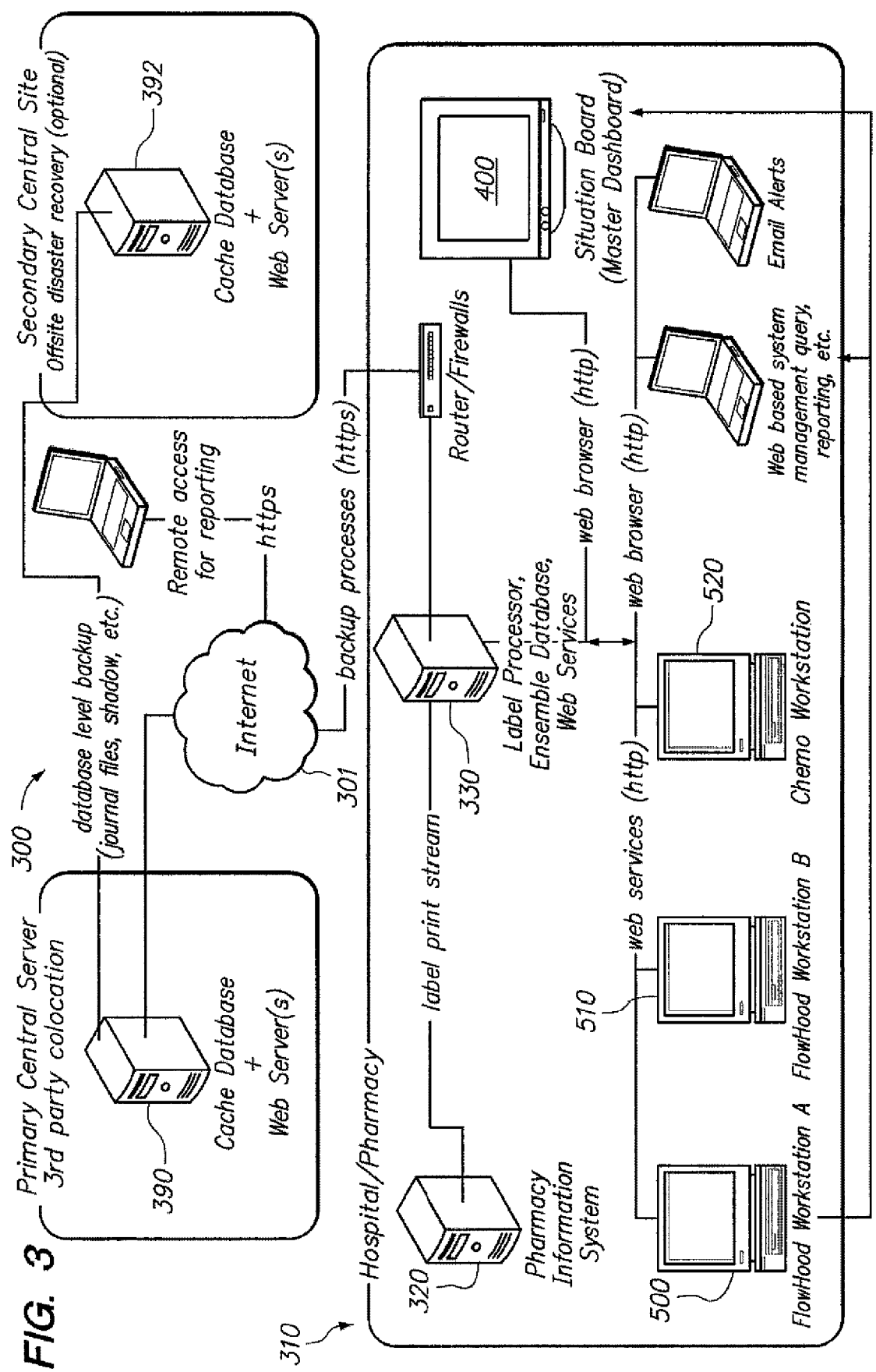
FIG. 3 illustrates an operating environment in accordance with an embodiment of the present disclosure.

By way of overview and example, a doctor or another person can enter one or more medication orders ("medication order") at a terminal in a hospital or a pharmacy 310, such as through a conventional pharmacy information system 320 as shown in FIG. 3. In addition, one or more medication orders can be entered through a terminal that is at a remote location and these orders can be delivered though a network (e.g., Internet), as described below, to a local server 310 (discussed below) where they are processed in the same manner as any orders entered directly into a terminal within the hospital or pharmacy.

When the order is processed by the pharmacy information system 320 and labels for the medication doses are generated, the data contained in the order and on the labels is captured, processed, and parsed by the computer implemented system to create individual medication dose orders ("dose orders") and associated database records. The software that operates in the local server 330 manages the dose-order processing and generates a dose order queue that can be sorted and/or filtered in any number of different ways as described below. The dose orders can be distributed to various compounding workstations such as workstations 500, 510, 520 in FIG. 3 (e.g., automated sterile compounding stations or manual processing stations) preferably in an optimized manner, as described below. At each stage of the dose-order processing, the database record associated with the dose order can be updated to reflect its status and location. Once the medication order is fulfilled, the resulting dose order is labeled, preferably at the dose preparation station so that the label is in close proximity to the prepared dose (as opposed to the conventional practice of centralized printing of all of the labels for dose-orders that enter the pharmacy), and more preferably is labeled so as to associate it with a patient care location. As described below, in one aspect of the present disclosure, a situation board 400 provides a view to all personnel in the pharmacy as to the status of each dose order record using metrics that have been established for display on the situation board.

In accordance with one aspect of the present disclosure, the dose orders that are received internally through terminals onsite or externally through remote terminals are all delivered and processed at a local server 330 that includes a label processing module, a local database, web services, and software for managing the status of the doses through the entire system. For example, the local database 330 can be hosted locally at a site, such as a hospital, and this local server stores a rolling cache of the current in-process work as well as a history of past orders (e.g., 30-45 day history). A situation board 400 is in communication with the local server and is configured to maintain a high-level view of the work that immediately instructs an observer regarding incomplete work and further allows identification of work that is pending, under preparation or prepared but not yet reviewed by a pharmacist. The situation board 400 can also maintain alarms for doses that are past due, as well as tracking doses whose preparation must be delayed because of limited stability in solution.

As mentioned, each dose order has an associated data record and the association in the data record can be a result of linking the interrogation of a scannable element to the dose order record. A code supported by or secured to the dose itself and a code associated with a bin at the dosage form's current location can both be interrogated and then that information uploaded to a database. For example, the codes can be bar codes and can be sensed using a bar code scanner. The particular "scanner" used and the manner of "scanning" can be varied within the context of the disclosure to suit the requirements of a given implementation. Thus, for example, the code can be an optically scannable bar code or an interrogatable code such as an RFID tag that is supported in lieu of or in addition to bar codes, plain text, or other codes. The terms "scanner," "scanning," and "scannable" are intended to include wireless interrogation or passive data reception whether they are based on an optical read, a radio frequency interrogation or an interrogation in some other frequency band, or a form of passive wireless data reception. More generally, the codes in scannable form are referred to as "tags."

As the dose is transported through the hospital to its final location, the bin can be scanned and any new location is scanned at various points to track its progress through the hospital.

Figure 1:
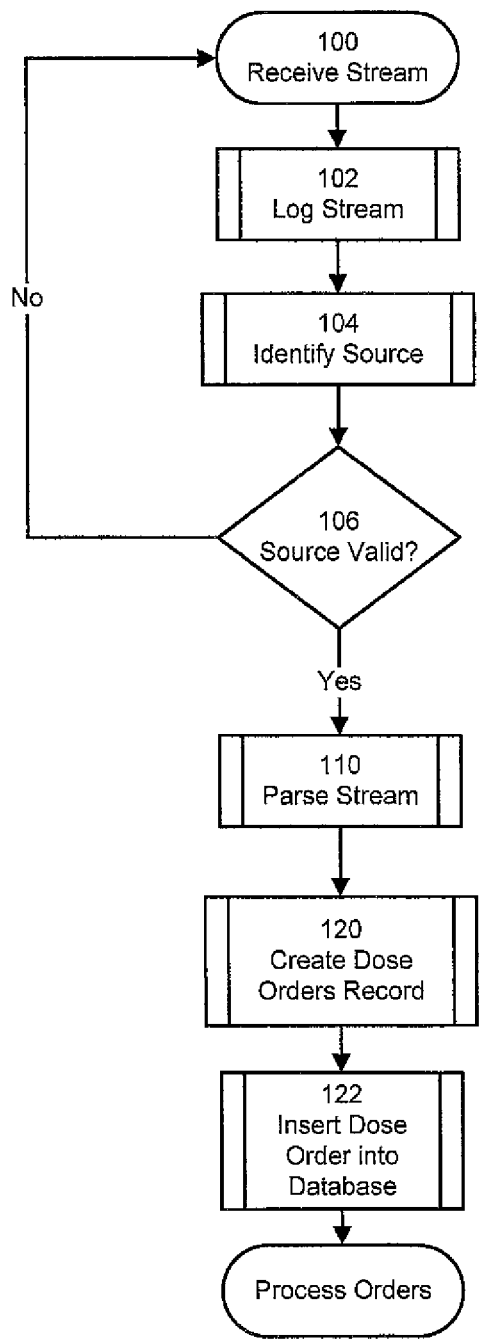
FIGS. 1 and 1A illustrate a process for receiving, processing, and preparing medication dose orders in accordance with one embodiment of the present disclosure.

With reference now to FIG. 1, a process is illustrated by which orders are received, processed, and distributed within the pharmacy or medication preparation center. At step 100, medication order streams are received by the pharmacy and are processed by a label processing module that comprises code that executes in a machine such as the local server 330 to perform the processes in FIG. 1. Order streams can be received through various methods. For example, a medication order can be entered into a computer terminal within the pharmacy itself, at a computer terminal in communication with the pharmacy over a local network, or at a device that is communicatively connected to the pharmacy from a remote location. Alternatively, the medication data can be captured by a monitoring module comprising computer code executing in the pharmacy for monitoring of, say, a port normally connected to a pharmacy printer, network monitoring for medication order information, or software application monitoring for events related to the input of medication orders. Traditionally these order streams represent data intended to be printed on labels on a printer, and oftentimes comprise serial data streams.

Medication order streams can contain a list of medication doses to prepare. Each dose order and dose is preferably associated with additional related data such as the patient for whom the medication is intended, by when it should be delivered, and to where it should be delivered. Further details can be associated with the medication including the prescribing doctor, the time and date the prescription was entered, the reason for medication, and other relevant information frequently recorded and associated with a prescription.

Data streams containing medication dose data are preferably logged at step 102 by a monitoring computer. Preferably, streams are logged in a database or other computer accessible medium. Logging data streams enables extensive auditing and monitoring of the pharmacy—or hospital—dispensed medication. Because all data is logged, preferably in its raw form when it is first received by the pharmacy, no information is lost, corrupted, or disassociated during the processing or distribution of the medication. If necessary, an audit can be performed manually, off-line, or by a separate software program to reconstruct the data stream and all processing that should have or did occur after the pharmacy received the data stream. Furthermore, the logged data can be analyzed with respect to dose order demand. The average volume, peak volume, and standard deviation of dose orders can be determined for various historical time periods (e.g., day of the week, month, last week, last month, etc.). Based on this analysis, decisions regarding the required staffing to fulfill the expected volume of dose orders can be made.

Preferably, the data stream has an identifiable source. The source can be explicitly identified within the stream of data, or it can be determinable by the fulfillment system. Source determination can include, for example, examining TCP/IP packet or its header/footer information, examining cryptographic signatures of the stream, or data retrieved through additional network communication requesting the source. The source is identified at step 104.

At step 106, the fulfillment system can be configured to determine whether the data stream originated from one of a set of valid sources. This can include identifying the source of the data stream and testing that it is one of the sources among those in the set. Validating the source ensures each medication dose prepared by the fulfillment system is legitimate and originating from an authorized prescribing entity. Alternatively, the validation can ensure that the prescribing entity is presently entitled to have its prescriptions filled by the pharmacy. If the source is not valid, the fulfillment system returns to step 100 to receive additional streams. Optionally, notifications can be sent to the source to inform it that there were validation issues or that the window for continued validation has one or more constraints (e.g., will expire in so-many days due to an overdue invoice).

In one embodiment of the fulfillment system, the software executes in a multi-threaded or multi-process environment. Thus, multiple streams can be processed simultaneously, by including necessary memory and database locks to ensure consistency. While the fulfillment system is described above as returning to step 100 to receive additional streams, persons of skill in the art appreciate that streams can be received by a server thread and dispatched for processing to other threads within a thread-pool. Other multi-threaded or multi-process mechanisms can be used to control the processing of data streams received by the fulfillment system.

After determining that the source is valid, the stream is parsed to extract relevant information at step 110. The fulfillment system can parse various message and data formats. Moreover, the parser can be extensible, such that as new formats are implemented or included within the networked environment, a parser extension can be included in the fulfillment system to parse the new format. For example, if the data stream is a serial printer data stream, the fulfillment system can determine the format of the data and pass the stream to the appropriate serial printer data parser. The printer data parser is configured to extract the dose medication contained within the stream. Preferably, the parser extracts all relevant data contained within the stream and maintains a record of the extracted data. The parsing methodology is preferably encapsulated in a library or set of modules that are called upon, as necessary, to parse a stream of any determined format. Each library entry or module operates as a "parser," as that term is used herein.

The data stream can contain one or more dose orders. For example, the stream may contain a single prescription dose request by a doctor for a single patient. Alternatively, the stream can include multiple dose orders for batch processing. The parser is preferably configured to recognize and discriminate between individual dose orders within a stream. The discrimination of individual dose orders can be accomplished by recognizing an order delimiter, or alternatively can be defined by the format of the data stream.

The data extracted by the parser at step 110 is used to create a dose order record at step 120. A dose order record is preferably created for each individual dose order encoded by the data stream, and contains the information extracted from the stream. At step 122 each dose order record can be stored in a database or other data storage system such as a suitable data-structure. Additionally, each dose order is preferably assigned a unique dose identifier that can be used to track the dose order and resulting dose through the fulfillment system.

A dose order monitoring application or module is operative at the local server 330 to track dose orders in the database and provide monitoring services such as to provide data that is displayed by the situation board 400. As such, at this stage, the dose order can be included in the presentation output on the situation board 400 to apprise persons in the pharmacy that another dose is in the queue for processing, and to apprise a supervisor or pharmacist of the change to the queue without requiring them to be in the pharmacy, as will be described further below.

The above description outlines the steps by which medication data streams enter the pharmacy and are pre-processed in anticipation of being filled by the pharmacy. Once the data streams have been processed, parsed into individual medication doses, and stored as dose records within the fulfillment system, the pharmacy can prepare the medication doses identified by each dose record at one or more workstations configured to permit preparation of medications, such as workstations 500, 510, 520.

In accordance with an aspect of the present disclosure the medication data streams can enter pharmacy through data entry at a local station or by being entered over a network at a remote location (see FIG. 3). The local server 330 includes a label processing module and a local database, for example, an Ensemble database). The local server receives dose-orders and performs the processing described above with reference to and illustrated in FIG. 1.

All dose orders are initially stored in the local database, such as the Ensemble database that is hosted locally at each site. A queue is generated for all received dose orders and, as described below, in accordance with one aspect of the present disclosure, the work order queue can be displayed on a touch screen display at one or more workstations.

Figure 11:
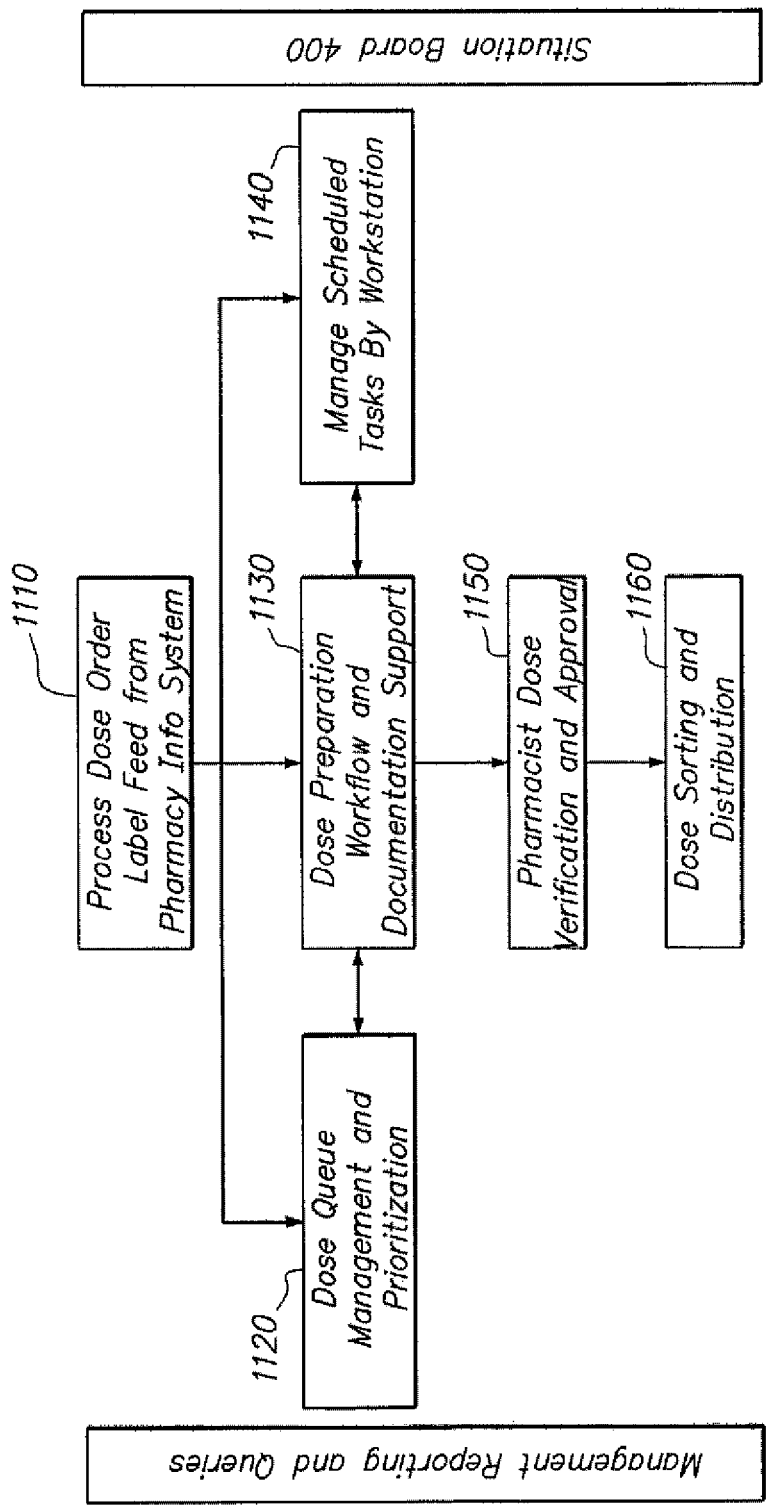
FIG. 11 is a schematic overview of management and reporting of medication preparations in accordance with a broad aspect of the disclosure.

With reference briefly to FIG. 11, an overview of the dose management process is outlined in broad terms. At block 1110, a dose order received from a pharmacy or hospital information system 310 is processed substantially as described in connection with FIG. 1. Those dose orders define respective records in the local server 330 that are forwarded to applications executing at one or more workstations located within the pharmacy, hospital, or elsewhere. This workstation application or the technician responsible for operating the workstation has access to a dose queue and can prioritize and manage does order processing, as indicated at block 1120. The workstation application or technician can manage the various open tasks (orders to fill) by interacting with the workstation in order to follow the protocol or "recipe" mandated for a particular dose order or batch of orders, as indicated at block 1140. The dose orders are prepared as final doses at the workstation with the benefit of documentation support, as indicated at block 1130. The document support is provided to the technician to guide preparation and better ensure that doses are prepared in accordance with established protocols and policies. As described further below, the intermediate steps in the preparation of each dose order are subject to data capture to permit post-preparation review of the steps taken to prepare each dose. Thus, as can be appreciated, blocks 1120, 1130, and 1140 are contemplated as being performed at one or more dose-preparation workstations. In the meantime, as schematically illustrated along the left and right margins of FIG. 11, the situation board 400 can present progress information and other metrics to assist in the orderly management of the pharmacy, while management modules can provide queries and report results of the progress as well as other metrics that concern the facility 310 as well as other facilities through an interface to the local server 330. At block 1150, the local server 330 receives through a connection such as a web service portal or other communicative link an approval or a denied message from a pharmacist upon his or her post-preparation review of the intermediate steps in the preparation of each dose order. At block 1160, sorting and distribution of the prepared medication doses to the intended recipient or for storage in anticipation of use completes the process.

Figure 1A:
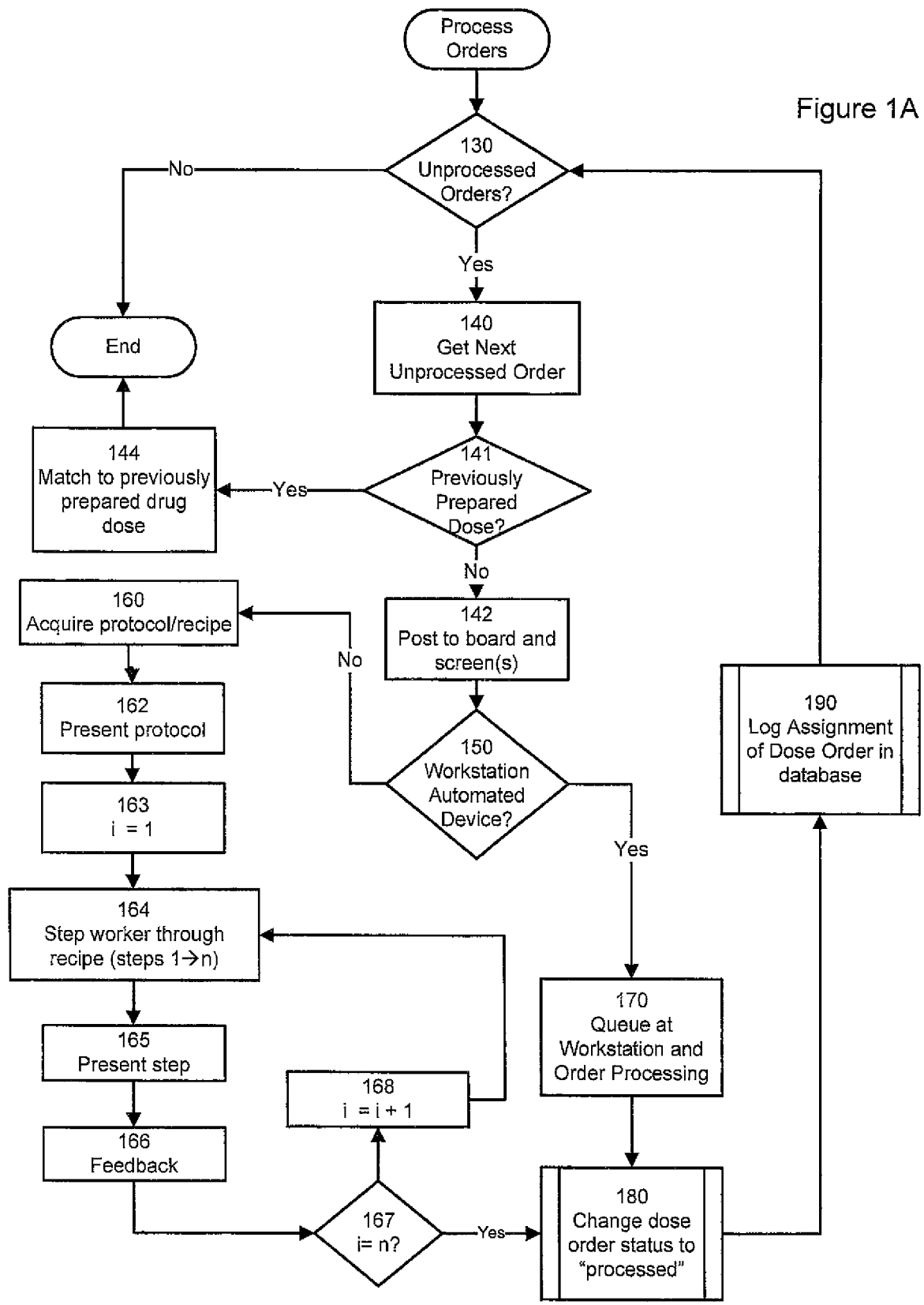

Referring now to FIG. 1A, order fulfillment processing commences at step 130 at which a fulfillment module determines whether there are any unfulfilled medication doses in the database. The fulfillment module comprises code executing in a machine, and, more preferably, within the local server 330, and the label processing module can be part of the fulfillment module or the two modules can communicate with one another in the processing of dose orders. If no unfulfilled orders exist, the fulfillment module can redirect its resources to processing incoming data streams at step 100, or completing or processing any active thread, as indicated schematically by the "end" terminator in the flow chart. However, if unfulfilled dose orders are in the database, the fulfillment module will retrieve an unfulfilled order at step 140. At decision 141, the fulfillment module can determine whether a dose was previously prepared and stored which would satisfy the dose order. For disclosure of a system that prepares dose orders in anticipation of need for such orders, see U.S. application Ser. No. 11/844,135, filed Aug. 23, 2007, entitled "Automated Centralized Preparation Of Medications In Anticipation Of Use," which is hereby incorporated by reference as if set forth in its entirety herein. If no such dose exists, the dose order can be posted to the work order queue at each workstation and is posted to the situation board 400 (sometimes referred to in the art as a "dashboard") at step 142. Optionally, the requirements for filling the dose order are retrieved and used to post the dose order to the work order queues of only those workstations that are suitable for handling such a dose order. In this way, individual workstations can have a tailored queue of pending dose orders. In another arrangement, such tailored queues are provided to the individual workstations but the operator of such workstation can expand the presentation to see other dose orders in the queue even if not suitable for handling at the operator's workstation.

Figure 6:
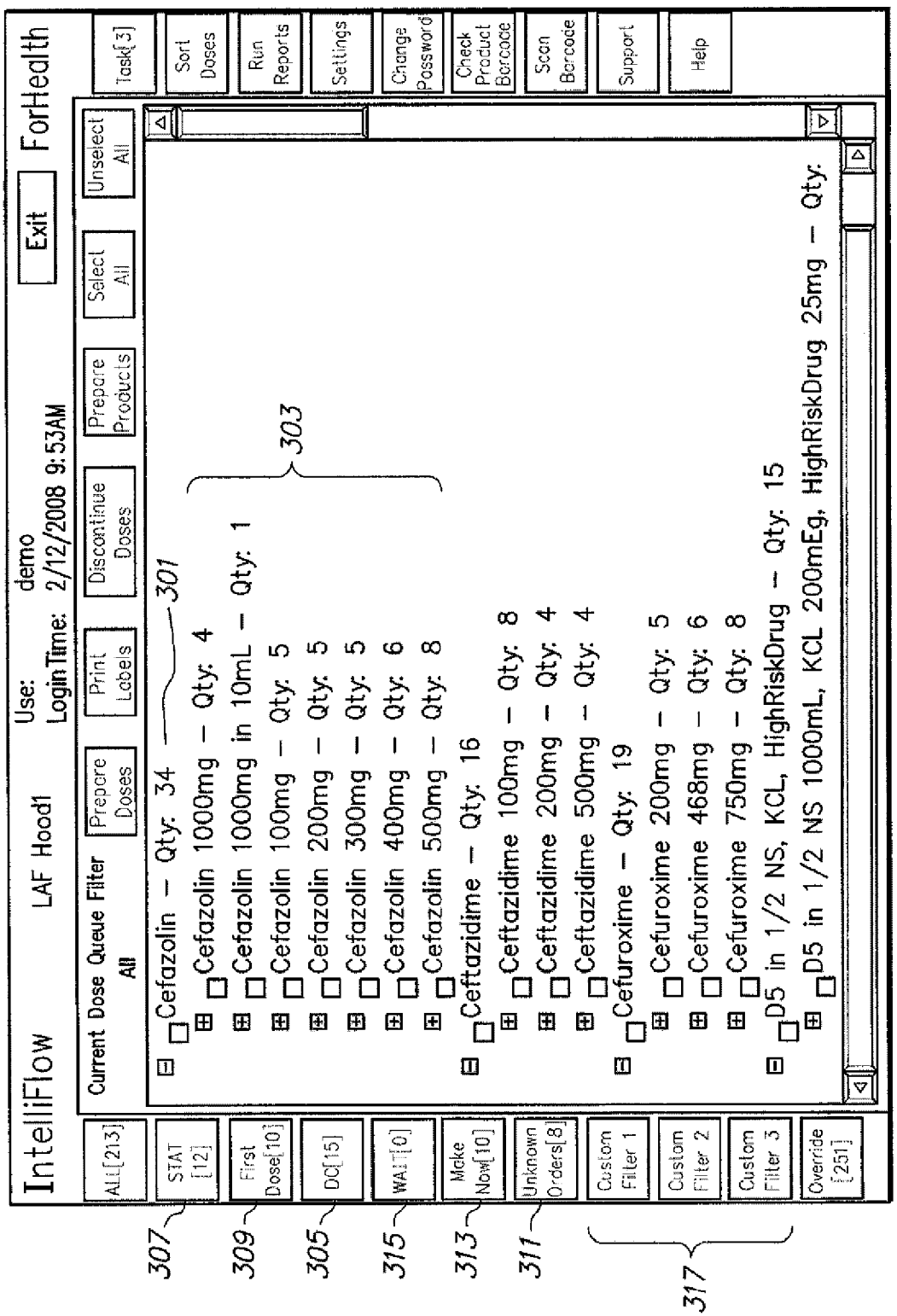
FIG. 6 is a dialog box showing an incoming, processed drug order that needs filling.

Referring briefly to FIG. 6, as previously mentioned, the dose orders are stored in the local database and are displayed on a display (touch screen) at one or more workstations. For example, each workstation can include a touch screen display that lists all received work orders and can include identifying information or icons or other indicia that indicate which workstations are capable of fulfilling the dose order.

An operator at a given workstation can thus view a running tally of received dose orders and can select the orders to be processed at his/her workstation. For example, the posted drug orders can be color coded or otherwise coded to indicate which workstation(s) is currently capable of fulfilling the order (assuming that all orders are displayed). As another example, there may be two workstations that are similarly equipped and one operator is principally responsible for filling certain medications unless the order queue for other medications becomes too large. An operator (technician) at any given workstation can thus look at the work order queue and select certain dose orders to process and fulfill. Once the workstation operator selects the work orders, as by highlighting them on the touch screen, the work orders are assigned to this workstation and the selected work orders can be eliminated from the work order queue or otherwise indicated as being selected and not pending and available for selection by another operator at a different workstation.

In addition, if a workstation is off-line for maintenance or the like, the dose order processor will not indicate that this workstation is capable of fulfilling the order and will not assign dose orders to this workstation until it is back on-line and is fully operational.

The work order queue can sort and display the dose orders in any number of different ways. For example, the work orders can be sorted and displayed by drug type and can be further sorted by dosage amount as shown in FIG. 6. The total amount of work orders for each drug can be displayed next to the drug name in a main banner 301 and then underneath the main banner, the various drug dosage amounts are listed along with the quantity of each that is currently needed (lines 303). For example, as shown in FIG. 6, the main banner shows that there are 34 orders for the drug Cefazolin and underneath, the various drug dosage amounts, such as Cefazolin 1000 mg; Cefazolin 100 mg; Cefazolin 200 mg, are listed along with the quantity that is needed for each.

Each dose order listing can be displayed in a different manner to indicate information that is intended and helpful to the operators at the one or more workstations that process and fulfill the dose orders. For example, on the left column of the screen that is shown in FIG. 6, a box 305 labeled "DC" stands for discontinued dose orders which are orders that have been discontinued for some various reason and therefore, do not need to be processed and fulfilled. The box can have an associated color, such as purple, that allows individual dose orders to be indicated as being discontinued and therefore, should not be selected for processing and fulfillment. For example, the Cefazolin 500 mg (Qty:8) dose order line can be displayed in purple, thereby indicating that this dose order is discontinued and should not be processed. Also along the left column are other status indicators, such as "STAT" 307, "First Dose" 309, "Unknown Drug" 311, "Make Now" 313 and "Wait" 315. These indicators can dictate a preferred order of selecting and fulfilling the dose orders. For example, "First Dose" can indicate the highest priority dose orders which should be selected first before another dose order, including those dose orders that are labeled "STAT". Meanwhile, the situation board (FIG. 5) provides an overview of the queue for all drug orders that are being handled.

In addition, other options available for selection by the operator at a station can be displayed, such as along the left column. For example, one or more filters 317 can be employed by the operator to filter the dose orders that are listed in the work order queue. The filter 317 can be selected among standard ones, such as a filter that lists only those dose orders that can selected and fulfilled by the operator at a given workstation or the filter can be designed to only show only those dose orders that are classified as STAT orders and/or those that are classified as First Dose orders. Alternatively, the filter can be a custom filter that is created and defined by the workstation operator.

Figure 5:
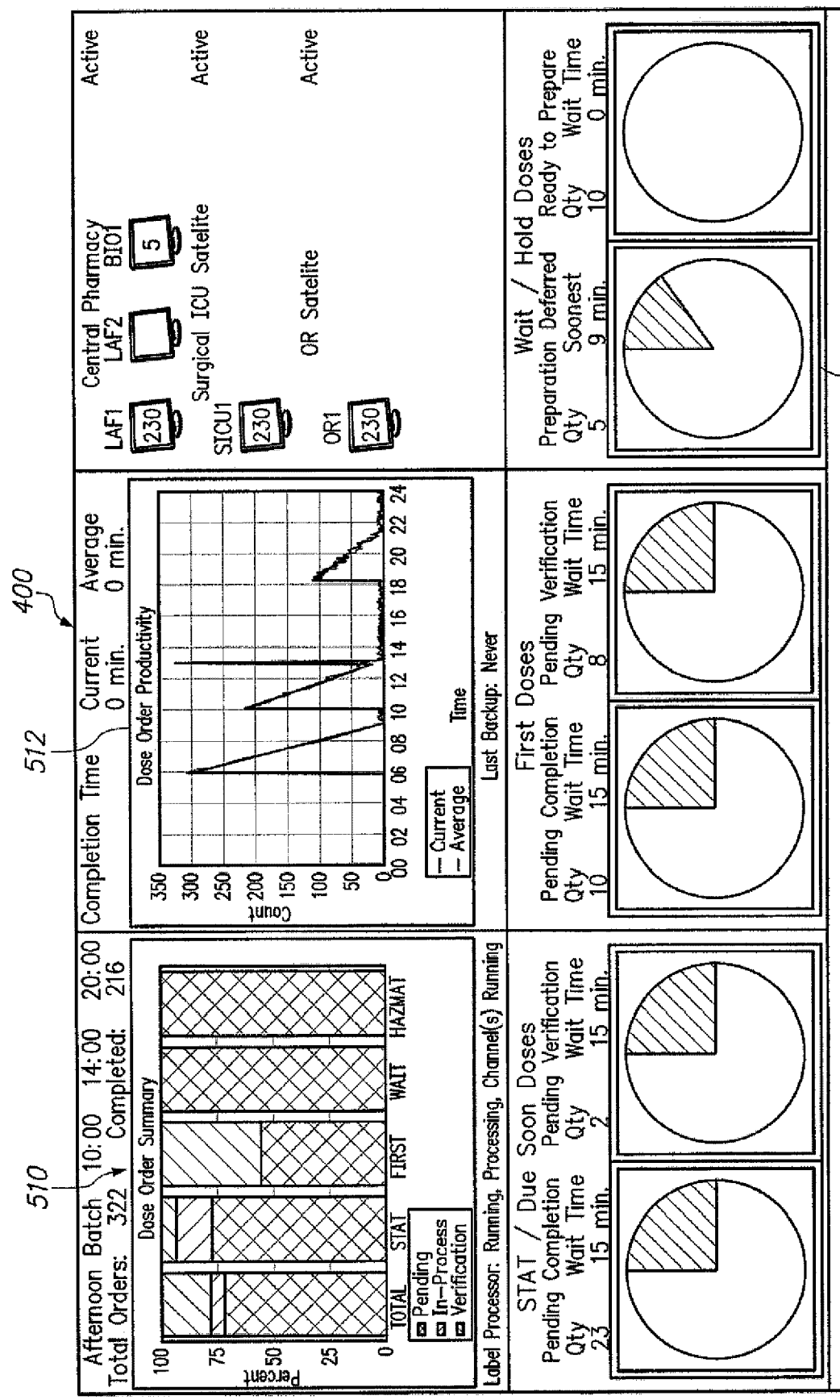
FIG. 5 is an exemplary display of a situation board that is part of the operating environment for displaying overall status summary information about current operations within the pharmacy.

Referring now to FIG. 5, the situation board 400 can be located at more than one location, such as at each workstation, as well as centrally within the pharmacy, and can be in the form of a browser-displayable "dashboard" that displays the overall status summary information about the current operations within the pharmacy (e.g., in the pharmacy IV room) through a conventional web-browser application such as Internet Explorer by Microsoft Corporation, Redmond, Wash. The situation board 400 can be displayed in the pharmacy on a large size, widescreen, flat panel display for high visibility and includes the count and percentage of doses awaiting preparation, in-process, or waiting verification. The situation board 400 thus lists all of the dose orders and permits operators at the various workstations to view all open orders and select orders as described below.

Dose order records stored in the local database can be ordered or arranged and displayed in the work order queue and/or at the situation board in accordance with a rule base that operates on the database with one or more rules. For example, one rule can be to optimize fulfillment of the orders. Thus, like dose orders can be processed at the same workstation one after another and hence faster because there is less cross-contamination and medication changes (i.e., retrieval and storage). Thus, dose orders can be grouped by type or medication, such that dose records requiring the same medication or with no risk of cross-contamination can be processed in order by the same machine, or set of machines. In this regard, the rules are configured to sort the dose-orders by type or medication. Alternatively, dose order records can be prioritized by urgency (e.g., "First Doses" or "STAT"). For example, if a doctor urgently needs a specific medication, the data stream identifying the dose can include information indicating its urgency, and the dose order record can include such urgency information. Thus, the rule in this instance operates to re-sort an urgent order to near the front of the queue, or have that order identified (e.g., flagged) as urgent for immediate or expedited fulfillment. Through this or a similar mechanism, the next unfulfilled dose order retrieved at step 140 can be arranged in the queue to optimize throughput or to satisfy other rule-based priorities. Alternatively and as described above, urgent orders can simply be highlighted and/or labeled as such in the drug order queue presented at the workstation.

At step 142, the drug order queue is generated and optionally one or more dose orders can be assigned to a particular workstation based on one or more rules that govern the distribution of dose orders to a particular workstation. The present system can be configured so that the server receives, stores, and parses the incoming dose orders (e.g., by using the label processing module and other software) and generates the work order queue that can then be posted at each workstation as well as at the situation board. The system can be designed so that the dose orders must be "pulled" from the work order queue, in other words, an affirmative step can be required for the dose order to be assigned to a particular workstation. For example, as discussed above, an operator at a given workstation reviews the dose order queue and then selects those dose orders that he or she will fulfill, e.g., by using the touch screen display, at which time, these orders are effectively assigned to the workstation and are removed from the work order queue.

In some instances the workstation is in the form of an automated device and therefore, the processor of the automated device has a selection module comprising code that causes a selection of those dose orders in the queue that can be fulfilled by the workstation. As discussed above, this selection can take into account a number of different rules including the number of pending dose orders at this workstation, the availability of different drugs, etc. The automated device communicates with the local server 330 and selects and pulls dose orders for filling.

However, even when the system is configured to operate in "pull" mode, the individual dose orders can be preassigned in the event that a dose order can only be fulfilled by a specific workstation, in which case the system recognizes this fact and identifies that this particular drug order is intended for delivery to that particular workstation. For example, if the dose order that is received and processed at step 141 is of a type that can only be fulfilled by a specific workstation (e.g., an automated chemotherapy workstation), the dose order will be identified as such on the work order queue and the workstation type that is qualified for receiving and fulfilling the dose order can be notified. Similarly, the type of dose order can be identified as a manual fill dose order on the situation board and one or more manual workstations can be alerted or can simply include the dose order on its screen.

Alternatively, the dose orders can be "pushed" to the individual workstations in that the local server selects which workstation is best capable of handling the incoming dose order and then assigns the dose order to the workstation. The dose order is then sent to the workstation for fulfillment of the order.

Furthermore, as dose orders are received and parsed 110 or processed 140, the system can analyze the supplies necessary to fulfill the order. The list of required supplies can be compared to an inventory of supplies and their availability, optionally broken down by hospital, pharmacy location, or workstation. If there are insufficient supplies, additional supplies can be automatically ordered or the relocation of supplies from one workstation to another can be ordered such that at least one workstation will have the necessary supplies to fulfill the dose order.

Each dose order record initially has an unprocessed status and is operated upon by a particular workstation that is selected to convert the dose order into a particular drug dosage form in fulfillment of the order. A workstation can be adapted for a particular purpose, such as to include automated pill counters, automated syringe preparation, automated intravenous compounding stations, or be configured for manual preparation. By examining the dose order record, the fulfillment system can determine the appropriate workstation among available resources to which the dose order can be assigned at step 142, in view of the dosage order itself or its urgency, that is, its priority requirement for completion. The workstation assignment can further consider the supplies required to fulfill the dose order and the supplies available at each workstation. Also, at step 141, by examining the dose order record, the fulfillment system can determine whether a matching dosage form has previously been prepared and stored, based on the contents of an inventory record, and used to fulfill that order, as indicated at step 144. In the event that a match is located, the further steps of FIG. 1A do not need to be performed in order to provide the source of the order with the requested dosage form; however, to prevent inventory depletion, the order can be processed at a priority (that is, in a time frame) that is less urgent than indicated in the order itself since the preparation of a drug dosage form based on the dose order is for the purpose of restocking the inventory. Also, in the event of a match, a person can be directed to a particular location associated with the drug dosage form so as to retrieve it from inventory, and the retrieval can be registered so that the inventory record can be updated to reflect that event. This is described in the aforementioned U.S. application Ser. No. 11/844,135.

It would be understood by one of skill in the art that the dose-preparation workstations can be located either centrally or in a distributed environment. Dose orders can be retrieved by or sent to workstations via standard data messaging techniques. A centralized environment allows for the pooling of resources. However a distributed environment allows fulfillment to be completed closer to the end user and can reduce some of the inefficiencies of centralization.

At step 150 each dose order record can be examined to determine if it is appropriate for an automated workstation, or an operation type of a selected workstation can be determined, for example, based on a flag, profile or other information associated with the workstation and interrogatable by the management module, such as workstation availability and its present set-up. If the dose order record is appropriate for automated fulfillment, the order can be queued at an automated workstation and processed at step 170.

On the other hand, and in accordance with a salient aspect of the present disclosure, if the dose-order is one determined to be suited for manual preparation, then the process flow branches to block 160. At block 160, protocol information is retrieved. This is because, before the dose order record is dispatched to a manual workstation for action by the operator, additional information is provided to facilitate the manual fulfillment of the dose order at the selected workstation. This can be based on the determination that manual preparation is required and the assumption that providing additional information can improve safety, efficiency, and precision during fulfillment of the dose order. The management module can associate the additional information with the dose order record. For example, at step 160 the medication and form of dose (e.g., syringe, IV, etc.) specified by the dose order record can be examined so as to determine the protocol by which the dose of that medication should be prepared. The protocol can specify the steps (e.g., sanitization and documentation) that must be taken during preparation to comply with Food and Drug Administration regulations or any other governing procedures regarding the conduct of the pharmacy. Furthermore, the protocol associated with the dose order at steps 160 and 162, preferably is interactive in guiding the operator through the fulfillment process to achieve the same level of accuracy and dose safety which is typically associated with the automation. For example, the protocol can require the operator's input including logging of events at critical stages of the dose preparation process (e.g., requiring the operator to scan information related to the source drug containers).

The additional information (i.e., protocol) can be associated with the dose order record at step 162 for presentation to the operator. The association can be accomplished by attaching the protocol file to the dose order record, or otherwise communicating it electronically to the workstation selected for handling that dose order, or by printing a copy of the protocol to include with a printed order for the dose. In a paperless environment, the protocol is preferably displayed along with the display of the order or can appear as a hyperlink or call-up dialog box from within the order display at the workstation.

The workstation can include various tools and monitoring equipment to assist and perform quality control during the manual preparation of the dose order. Such tools and monitoring equipment can include barcode scanners, digital cameras, scales, hydrometers, spectrometers, and other tools that can be used to verify the properties of a substance. For example, a computer monitor at the workstation can prompt the operator to take certain measurements of the dose order being prepared and input the results of those measurements. Failure to input a measurement within an acceptable range can result in the system automatically rejecting the preparation. Furthermore, to prevent operator fraud, the system can prompt the operator to place the preparation on a scale, or within another instrument, that automates the measurement, thereby reducing the opportunity for the operator to intentionally or unintentionally deceive the system. In this regard, it should be appreciated that the protocol presented to the used at block 162 is preferably coded to capture the progress made toward dose fulfillment. Thus, steps taken in completing the protocol or recipe are preferably coupled with specific operator input such as photographing a drug vial, weighing a syringe, and the like, with the inputs being captured and included in a data record that can be forwarded to the pharmacist for review and approval. The data record can be a record storable in the Ensemble database that is used in a preferred embodiment of the disclosure.

As noted, one form of data capture during order preparation can be the capture of images of the medication source(s) used to prepare a particular dose. That is, a digital camera can record an image of each medication source, individually or together, that is used to prepare the dose. The image preferably displays the identification of the type of medication, its lot number, expiration date, and other quality control information that went into the final dose that is later submitted for pharmacist approval. The image(s) can be stored in the database or otherwise associated with the data record for the prepared inventory dose, and by accessing the dose order and the images associated with the prepared dose, from either a local or remove terminal/computer, a pharmacist or other authorized and qualified individual can verify that the correct medication sources were used to prepare the inventory dose.

Quality control can also include the recordation and logging of any technician or operator involved in the preparation of a dose order. The identity of the technician or operator can be recorded by fingerprint, key-card, username, password, or other known methods of identification. Additionally, quality control tasks can be assigned to specific workstations or operators, such as supervisors or quality control specialists. All of this information can be stored in the same data record as the medication dose, or in a different record that includes a link or information that permits association with the medication dose.

In one embodiment of the present disclosure, step 162 involves presenting the protocol to the operator in the form of a number of steps that must be performed in order to prepare the dose. As the operator performs each step or selected steps, verification that such step was performed must be entered by the operator or otherwise be confirmed by equipment that captures certain information presented by the operator. If during any step, a verification error arises and there is a question as to whether the step was properly performed, the dose order processing is prevented from continuing to the next step until the step is verified as being properly performed or until the dose order is flagged as being not completed due to an error. If this occurs, the operator can then receive the next dose order in the work order queue for that particular workstation and start the dose preparation process for this new dose order. Thus, step 162 is akin to presenting the operator with a recipe except that several if not all steps that are performed have the operator interrogated to provide information that better ensures that each step was performed in accordance with the protocol. As discussed below, certain steps can be recorded by using one or more cameras or other equipment and thus, a record is compiled and saved for each dose order in case there is every any question as to the integrity of the dose order and whether an error was made in processing the dose order.

Figure 10:
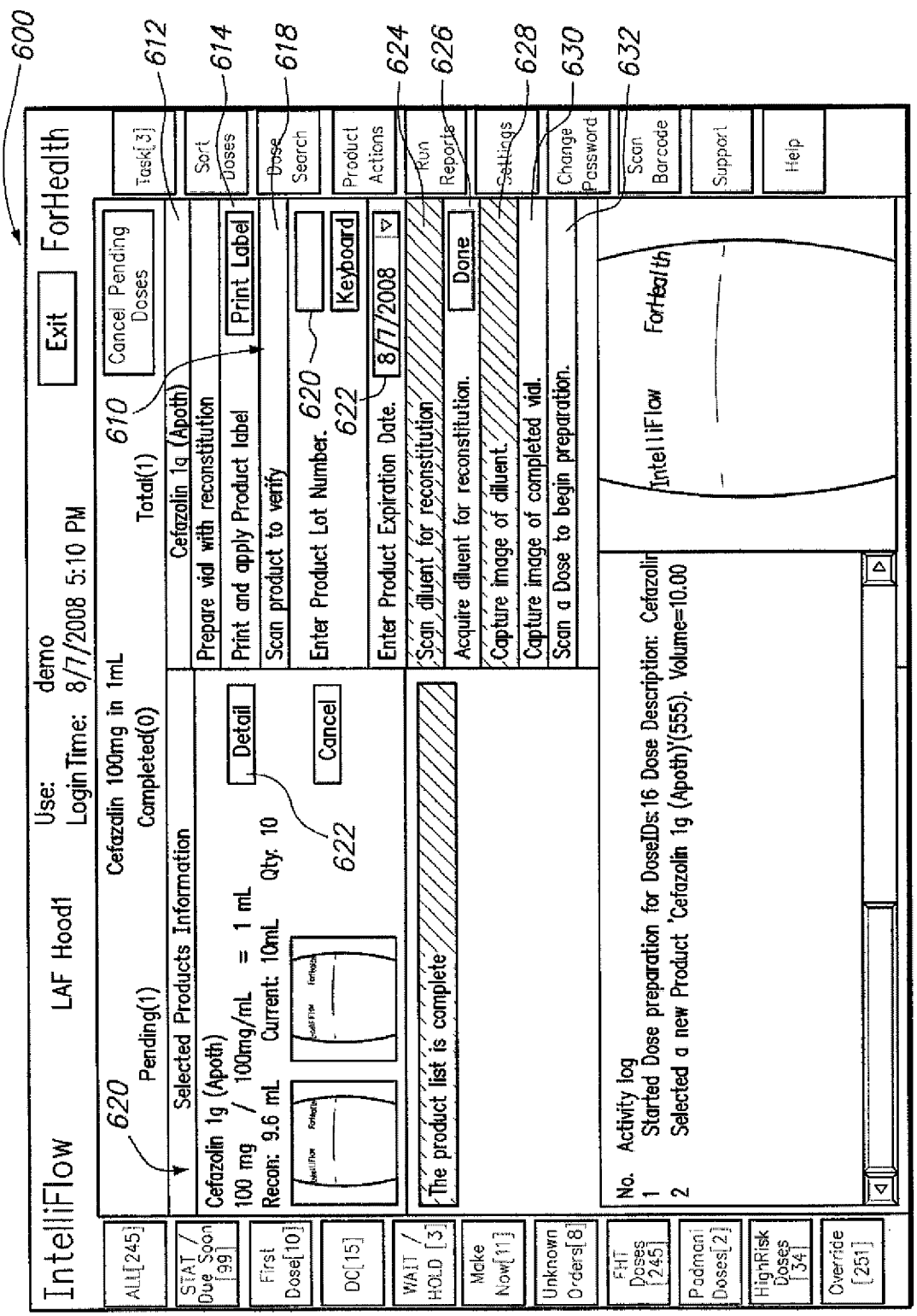
FIG. 10 is an exemplary display of a product preparation screen and procedure.

Referring briefly to FIG. 10, one exemplary screen 600 is illustrated that lists a number of steps generally indicated at 610 that are required to be performed to successfully prepare a medication product that is used to prepare a dose that is part of a dose order. On the left side of the screen, the drug to be prepared is clearly identified at 620, in this case Cefazolin 1 g (Apoth). This screen is an interactive screen in that the user can simply highlight different areas either to receive more information or to enter information. For example, there is a Detail button 622 near the drug identification and if additional information is needed concerning this particular drug order, the user can simply highlight this particular button (as by "clicking" the box).

On the right side of the screen are processing steps 610 that must be undertaken in order to prepare the requested dose. For example, a banner 612 indicates again the drug being produced is Cefazolin 1 g (Apoth) and below this banner there are a number of steps 610 that must be performed in order to produce the correct dose (drug product). The illustrated screen shows a first step 614 of printing and applying a product label. The label is printed by simply pressing the button 616 that is labeled "Print Label". As soon as the label is printed, the user is prompted to move on to the next step 618 which is a step of scanning the product to verify that the proper product is present at the workstation. Conventionally scanning equipment can be used to scan (e.g., a barcode) the product and then the user is prompted to enter the Product Lot Number in a box 620 that is provided and the user then enters the Product Expiration Date in another box 622. All this inputted information is used to confirm that the correct product (drug) is present and is being used in the preparation of the Cefazolin 1 g dose.

In another aspect of the present disclosure, other identifying information can be used to assist in determining that the correct drug is present at the workstation and is suitable for use in fulfilling a pending drug order. More specifically, the Drug Listing Act of 1972 requires registered drug establishments to provide the Food and Drug Administration (FDA) with a current list of all drugs manufactured, prepared, propagated, compounded, or processed by it for commercial distribution. The National Drug Code (NDC) is a universal product identifier used in the United States for drugs intended for human use. The FDA inputs the full NDC number and the information submitted as part of the listing process into a database known as the Drug Registration and Listing System (DRLS). The information submitted as part of the listing process, the NDC number, DRLS, and the NDC Directory are used in the implementation and enforcement of the Act.

The National Drug Code is a unique 10-digit, 3-segment number assigned to each medication listed under Section 510 of the Food, Drug, and Cosmetic Act. The number identifies the labeler or vendor, product, and trade package size. The first segment (the labeler code) is assigned by the Food and Drug Administration. A labeler is any firm that manufactures, repacks, or distributes a drug product. The second segment (the product code) identifies a specific strength, dosage form, and formulation of a particular firm. The third segment (the package code) identifies package sizes.

The official format of the NDC code is a 10-digit number that can be presented in one of three formats:
1) 4-4-2=1234-5678-90
2) 5-4-1=12345-6789-0
3) 5-3-2=12345-678-90

When presented electronically, the NDC number is presented as a 10-digit, unformatted number (such as in a bar code). The 10-digit, unformatted number can be accessed and used as part of an automated drug preparation system in that this number can be used to locate drugs that are stored at a storage location. However, when presented in print, the NDC number is presented as a 10-digit formatted number as shown above. Consequently, a drug label on the chug container will typically have the formatted NDC number.

Recently, the format of the NDC has been revised and changed so that it includes 11 digits as opposed to 10 digits. The new 11 digit NDC number has a 5-4-2 format. More specifically, database vendors, CMS (Centers for Medicare & Medicaid Services), and recently, the FDA are now using an 11-digit unformatted number that is intended to remove ambiguity between the three formats that were previously used for 10 digit NDC numbers. Since many drug preparation systems, including the present one, purchase formulary data from a vendor (e.g., Multum), the 11 digit unformatted form of the NDC data is automatically provided in the formulary when the formulary is loaded into the drug preparation system. Conversion from the digit code to the 11 digit code results from the proper placement of a zero. More particularly, the 11-digit code is created by adding a leading zero (0) to the field (in the 10 digit code) that has too few digits. The table below shows the transformation.

| 10-digit formatted | Format | 10-digit unformatted | 11-digit formatted | 11-digit unformatted |
| --- | --- | --- | --- | --- |
| 1234-5678-90 | 4-4-2 | 1234567890 | 01234-5678-90 | 01234567890 |
| 12345-678-90 | 5-3-2 | 1234567890 | 12345-0678-90 | 12345067890 |
| 12345-6789-0 | 5-4-1 | 1234567890 | 12345-6789-00 | 12345678900 |

The conversion between the 10 digit unformatted NDC number to the corresponding 11 digit unformatted NDC number or vice versa is complicated and there is no reliable conversion method since there is no way in positively telling where to add a zero (0) or which zero (0) is to be either deleted. The only reliable manner to transform between a 10 digit format and an 11 digit format is to start with the 10 digit formatted number.

Figure 12:
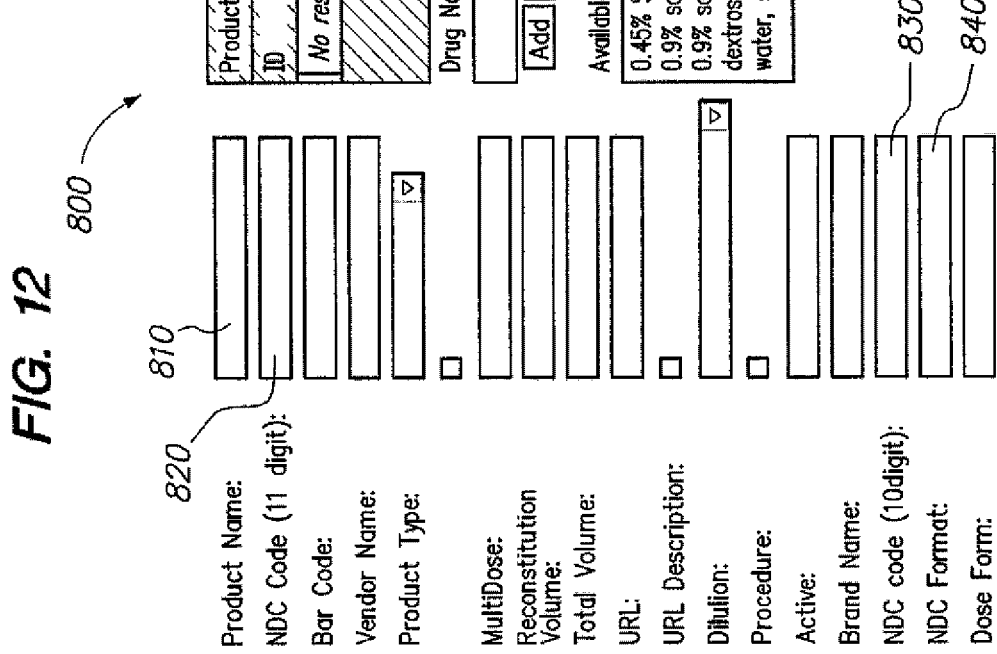
FIG. 12 is an exemplary display of a product information screen.

In accordance with the present disclosure and as shown in FIG. 12, an interface of the present system can include areas where NDC information is inputted, For example, a product information screen 800 is shown in FIG. 12 and includes a number of input fields (input boxes with or without pull down type menus) where a user can input certain product information. It will also be appreciated that some of this information can be inputted using a reader devices, such as a barcode reader, etc. Part of the product input information includes NDC related information. For example, in FIG. 12, the product information screen 800 includes a product name field 810; an NDC code field 820 that contains the unformatted 11 digit NDC number; an NDC code field 830 that contains the unformatted 10 digit NDC code, and an NDC format field 840 that contains the 10-digit format (i.e., 4-4-2, 5-4-1, or 5-3-2). By storing the 10 digit unformatted NDC code, conversion to the 11 digit format is possible. In addition, by storing, the NDC format at field 840, the integrity of the conversion process is ensured.

By inputting and storing the above information, the present system is capable of handling requests and requirements from entities, such as CMS, that require 11 digit NDC codes. In addition, by storing the 10 digit NDC code, the present system and the formulary stored therein, can process and communicate with third party systems that require the 10 digit NDC codes. As new CSP/drugs are added to the formulary (e.g., by loading formulary updates), both the 10 digit and 11 digit NDC codes are updated.

In accordance with the present disclosure and as previously mentioned, the present system includes means, such as readers and the like, which allow a particular drug to be identified at step 618 and compared to a database to ensure that the identified drug is the drug which is being requested is the same drug which has been identified at a particular location (station) of the present system. Since the NDC includes product code information, such as the specific strength, dosage form and formulation, it can be used in drug identification step 618 of the present system. It will also be appreciated that the NDC number can provide a means for redundantly confirming the identification of the drug being used at the work station to prepare the requested drug order. In other words, other identifying information that is printed or otherwise present on the drug product can be read and then the NDC number can be read and the two compared as part of an integrity check to ensure that the correct drug product is present at the workstation.

The next step 624 involves scanning the diluent that is used in the reconstitution process. Once again, conventional scanning or imaging techniques can be used to identify and confirm whether the correct diluent is being used in the reconstitution process. The step 626 involves acquiring the diluent for the reconstitution and then confirming its proper identity and the user can indicate that the step has been completed by pressing the button labeled "Done". The next step 628 can involve capturing the image of the diluent using conventionally techniques (e.g., a camera) and additional steps that can be performed are capturing the image of the completed vial 630 and scanning a dose to begin preparation of the individual dose 632. All of the information that is gathered in each of the steps is stored in the local database, preferably in the same record as or in association with the particular drug order being filled.

At any point, if a task performed in one of the steps is not verified as being correct, the operator is prevented from going onto the next step and the dose is not prepared.

Figure 9:
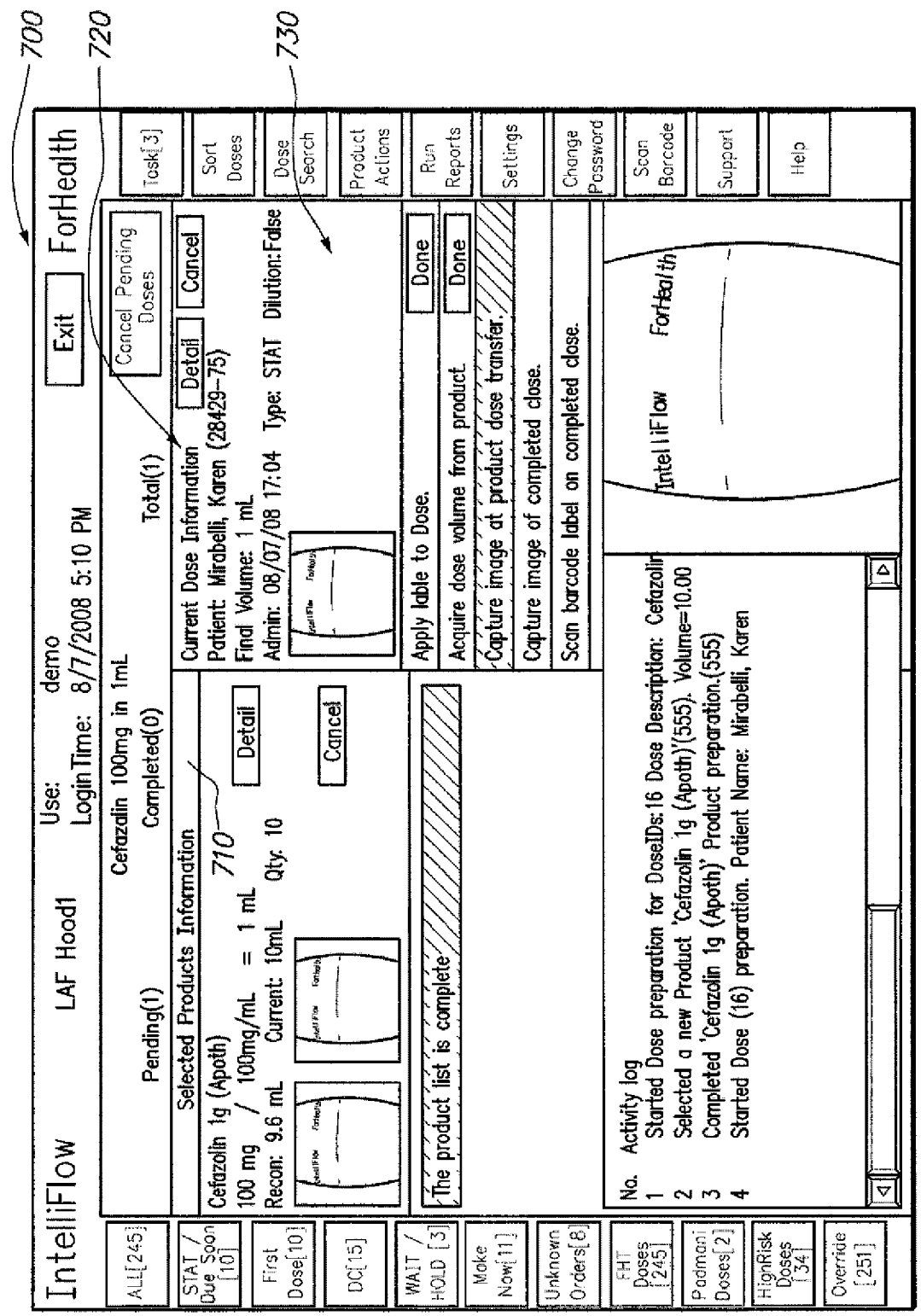
FIG. 9 is an exemplary display of a dose preparation screen and procedure.

Also, with brief reference to FIG. 9, a sample screen 700 shows exemplary steps that are displayed to the operator to assist the operator in preparing a specific dose of medication. On the left side of the screen, a "Selected Products Information" section 710 is provided and lists the drug product that is being prepared. In this example, the drug product is Cefazolin 1 g (Apoth). On the right side of the screen is information 720 that relates to the current dose that is being prepared for a specific patient. For example, the patient's name (e.g., Karen Mirabelli) is clearly identified along with any identifying patient information (a patient number). The dose information also includes a final volume of the dose (e.g., 1 ml) and administration information is provided, such as a date and time (e.g., Aug. 7, 2008 17:04) when the dose is to be administered. The type of dose (e.g., STAT) can also be listed to alert the operator to any special processing information (e.g., the dose should be processed in an urgent manner).

The screen of FIG. 9 lists a number of steps 730 that are to be performed by the user to prepare the dose and fulfill the dose order. For example, one step may be the step of applying a label to the dose and once this task is performed, the user can indicate so by pressing a button that is labeled "Done". Another step can be to acquire the dose volume from the product and once this task is performed, the user can indicate so by pressing a button that is labeled "Done". Other steps that are to be performed and verified are capturing the image of the product dose transfer; capturing the image of the completed dose; and scanning the barcode label on the completed dose. Each of these steps must be verified as being properly completed before the user can continue with the other steps of the dose preparation process.

The NDC information also contains formulary information and this can be used at the workstation as the drug is being prepared in accordance with the steps shown and described with reference to FIG. 9. In particular, this information can be used as part of an integrity check (drug verification process) to ensure that the drug is being prepared properly.

Referring again to FIG. 1A, the steps presented to an operator at a workstation generally include a number of steps. At step 163, a counter is started to make sure all N steps are performed. The value (i) is equated to 1 at step 163 and in step 164, the operator is stepped through the recipe (protocol) where the recipe includes steps 1 to N. In step 165, the operator is presented with a step to perform (namely, step i). At step 166, the operator must present some type of feedback (e.g., capture an image or scan a barcode) or confirm that the action requested at block 165 has been performed. If the feedback confirms that the step 165 was properly performed, then at block 168, a comparison is made between the value of i and N and if i=N, then the order has been filled and the flow proceeds to step 180, as described below. On the other hand, if i does not equal N, the process flow proceeds to block 167, where the value of i is incremented (e.g., by 1 as shown (i=i+1), and then the process flow loops back to step 164 so that the operator can be presented with the next step of the recipe. The steps 164 to 168 are performed until i=N which indicates that all steps have been completed.

As mentioned above, if it is determined at step 150 that the dose order record is suitable for automated handling, it will be queued at an appropriate automated workstation. Queuing the dose order record at a workstation presents a further opportunity to optimize the distribution of orders within the pharmacy. For example, it may not be feasible to determine at step 140 an optimal organization of dose order records to ensure that dose order records requiring similar medications are queued at the same workstation. Thus, at step 170, a particular dose order can be queued at an automated workstation that is known to be processing the same medication, or to any workstation at which a dose order involving the same medication was just queued (e.g., a workstation to which the dose order and protocol are provided at block 160. Re-ordering and queuing of dose orders can be very flexible if the urgency of the dose order is very low. For example, the dose orders can be queued in a less than optimal order with respect to time, but more efficient with respect to medication changes and cleanings to prevent cross-contamination. Optionally, the current workload and/or work distribution of dose orders to workstations can be tracked or monitored and presented to a user (e.g., presented on a centralized display) for management and performance monitoring.

Moreover, various quality assurance activities can be assigned to workstations. These activities can include mandatory cleaning, training sessions, or inventory procedures. They can be scheduled at a workstation based on necessity (e.g., if the workstation is determined to be "dirty"), passage of time (e.g., protocol can call for cleaning or training every two hours or two days), or by need (e.g., monitoring procedures determine that certain equipment is "dirty" or that a particular operator is making mistakes and requires additional training). As used herein, "dirty" refers to a station being in a queue for a cleaning.

Once the workstation fulfills the dose order, the status of the dose order record can be changed to indicate that it has been processed at step 180. The status change can be received by the fulfillment system as an acknowledgement that the drug dosage form has been prepared, or as a "processed-order" status, and this can further result in an update to the dose order record, the inventory record, or both concerning any drug dosage forms that have been prepared but not yet delivered. Additionally, data concerning the assignment of the dose order to the selected workstation and the completion of the dose order can be logged in the database. Logging information concerning which workstation processed the dose order into the database (e.g., an Ensemble database), as indicated at step 190, enables complete tracking of both the dose-order processing steps and tracking of the prepared dose itself from its entry as data into the pharmacy system to its delivery to the patient. Accordingly, at step 190, the information can be logged into the Ensemble local database and the situation board updated to show completion of the drug order. The situation board thus provides an updated tally on current drug orders being processed and historical information on processed drug orders, thereby affording the pharmacy and workstation operators hands-on access to performance data and other relevant information concerning the dose orders that are being requested for fulfillment.

The foregoing discussion details the process by which a data stream containing medication dose order information enters the pharmacy and is processed by the local server 330 (which includes a label processing module, a database such as the Ensemble database mentioned above, and web services) and filled so as to produce the requested pharmaceutical dose. The fulfillment system is further capable of responding to any status inquiries concerning a given dose order with order status (e.g., "unprocessed," "in-progress at {selected workstation}," "processed" and the like) and optionally a location (e.g., in bin A, on cart B, in pediatric ward, etc.). The fulfillment system is also capable of monitoring and tracking the prepared dose through to its delivery with additional status information (e.g., dispensation to patient {X} s), as discussed next with reference to FIG. 2.

Figure 2:
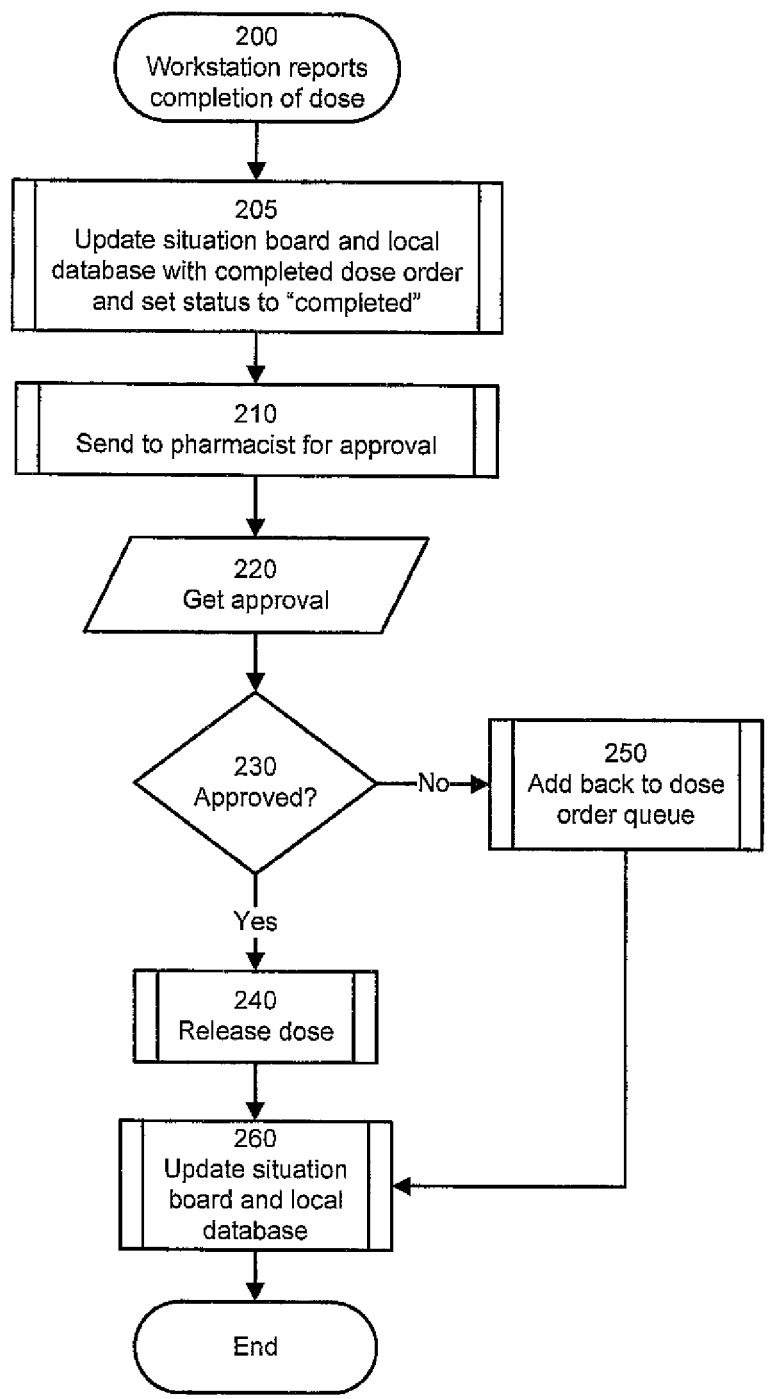
FIG. 2 illustrates a process for managing, approving and distributing prepared medication doses in accordance with an embodiment of the present disclosure.

Referring now to FIG. 2, a process flow is illustrated that commences when a workstation identifies a particular dose as having been completed, as indicated at terminator 200. The local database is updated with completion information at step 205, and this provides status information that can be referenced by persons outside of the pharmacy in response to a status inquiry and by the system in managing the distribution of subsequent dose orders. The identification preferably associates a unique identifier with the dose. The database record associated with the identified dose can be marked as completed. Alternatively, various other subsystems can be notified of the completion of the dose. For example, a storage subsystem that tracks medication that is "on-hand" can be updated with the prepared dose's record. Additionally, a delivery subsystem can be notified that the prepared dose is completed and ready for delivery to its destination. At a later time, for instance, according to a schedule, the information in the local database can be uploaded to a central server 390 that can be configured to communicate with the respective local databases of multiple pharmacy systems.

At step 210, the completed dose order is sent to a pharmacist for approval to allow the dose order to be released if it is verified. At step 220, the pharmacist is presented with the information necessary to decide whether the dose order should be approved. If the pharmacist is on-site, the pharmacist can visually inspect the dose order and if the dose order was manually prepared, the pharmacist can interview the clerk who filled the dose order in order to verify that protocol was properly followed. If the drug order was prepared by an automated system, the pharmacist can review the associated records of the dose order that were generated by the automated drug preparation system during the processing of the dose order.

Another aspect of the present disclosure is that it provides a portal for remote inspection of prepared doses and thus facilitates the practice of telepharmacy, by which a pharmacist can inspect the dose preparation from any location inside the hospital or elsewhere so that doses are released more quickly and efficiently. Accordingly, dose inspection/verification can be performed by a pharmacist from any location using the portal of the present disclosure. Dose information such as can be collected and stored as the recipe or protocol for order fulfillment is performed, and any images that have been captured (see FIGS. 7 and 8) are presented to the pharmacist for inspection and approval. Images, such as those in FIGS. 7 and 8, can be presented through a conventional browser, optionally with the use of a plug-in or other active code that provides magnification, rotation, contrast, and other adjustments for closer inspection.

The pharmacist can thus look not only at images of the final product, including the product label, and other related product information, such as barcode information, but also, the pharmacist can review information and images that are obtained at particular steps in the overall drug preparation process. For example, during a drug reconstitution process, the operator is stepped through the drug preparation as described above and must confirm that each step was successfully completed. One of the steps is the selection of a particular drug vial and this event can be captured using a camera to produce an image that can later be reviewed by the pharmacist or a scanning event by which the operator identifies the drug vial being used. The pharmacist can view each or many of the steps that was taken in order to confirm that the step was properly completed and thus, the dose was properly prepared. Many times in a pharmacy, a clerk is working under the supervision of a pharmacist and it is the clerk that actually processes the dose order. Thus, in the event of any questions about an order, the pharmacist is limited to speaking with the clerk. This aspect of the present disclosure offers a superior and more complete way of inspecting and verifying the drug order in order to release it to the patient since the pharmacist can visually inspect the different, multiple images and/or data obtained during the various steps of preparing of the drug to confirm that the steps where carried out properly and thus, ultimately conclude whether the dose order was properly prepared and should be released to the patient.

This can be important in many circumstances, including when the constituent components of the final dose include more than one clear fluid such that a visual inspection of the final dose cannot provide a basis for the pharmacist to confirm the accuracy of the dose. Thus, a benefit results from the capture and review steps described above, regardless of whether the pharmacist is on-site or remotely situated.

Figure 7:
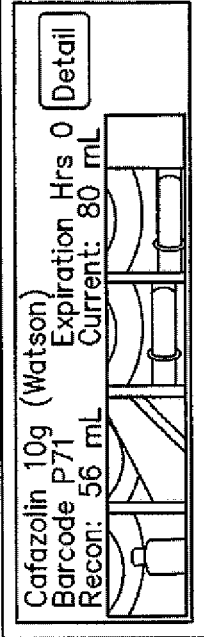
FIG. 7 is a dialog box showing details concerning a preselected drug order.
Figure 8:
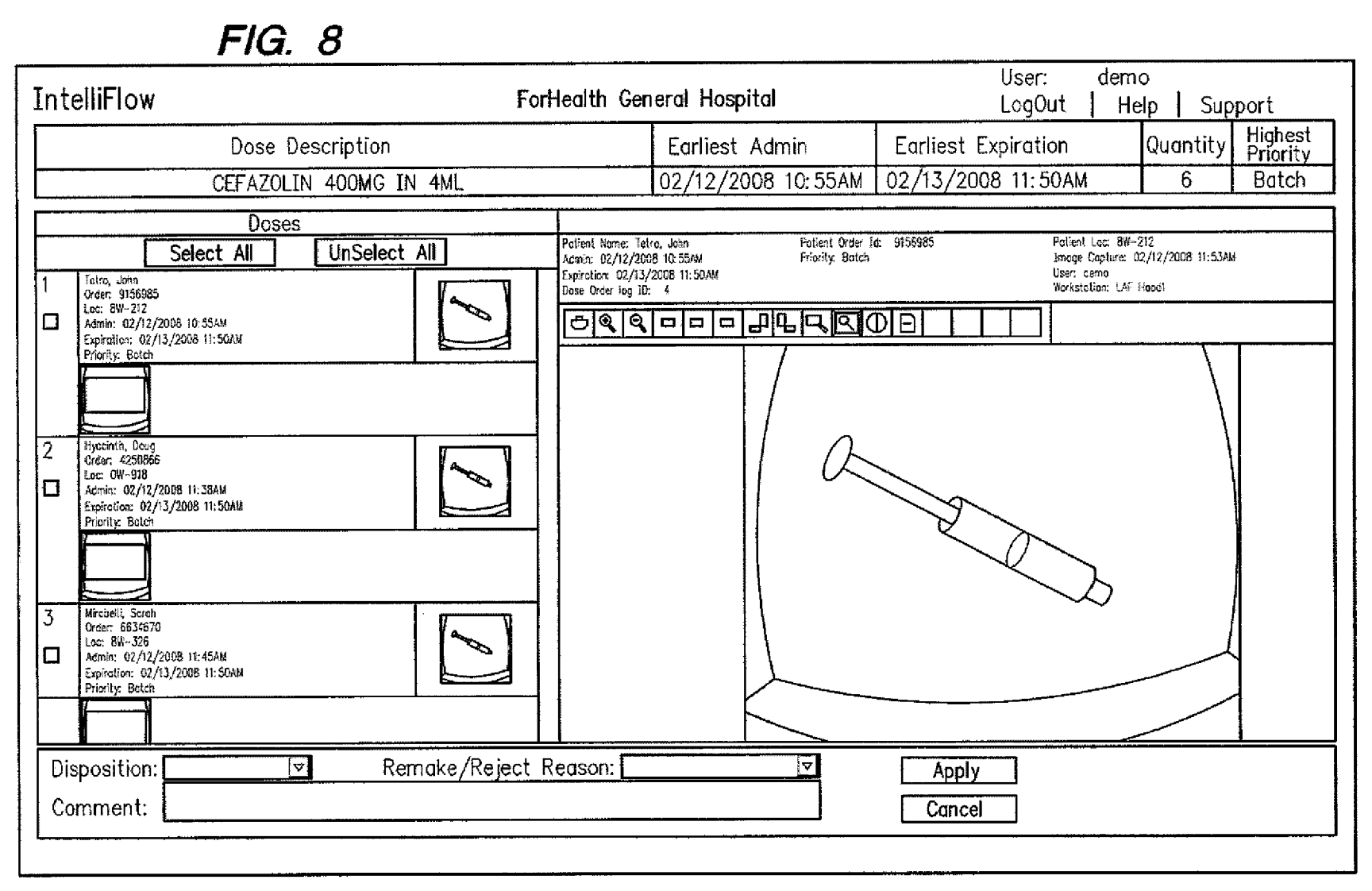

FIGS. 7 and 8 show the various images that can be selected by the pharmacist in order to view the final dose order, in this case a syringe filled with medication. Different angles and different views are available to the pharmacist, as well as information that has been captured in other ways such as by scanning or weighing steps, if called for in the recipe at the workstation that prepared the final dose being inspected.

Preferably, the local server 330 includes web services or a communication module that enables the data records associated with the dose order and its production to be viewed through a conventional web-browser program. As such, the pharmacist no longer has to be physically within the pharmacy to inspect and verify dose orders and ultimately either approve and release the dose order or reject the dose order. The opportunities that this system presents are varied and great. For example, a number of pharmacies can subscribe to a service where pharmacists inspect and verify dose orders from a remote location, either all the time or after the close of normal business hours. In addition, when the drug orders are prepared by automated drug preparation devices as opposed to pharmacy clerks, the inspection and verification process can be outsourced to one or more pharmacists who review and verify the dose orders.

In addition, a panel of pharmacists can, at one or more remote locations, review the dose orders that have been prepared by a number of different workstations (both automated and manual), regardless of the location of such workstations. Each pharmacist can review all of the digital records and stored information as described above as part of the inspection process and then can approve the dose order for release if the pharmacist concludes that the dose order was properly prepared. The approval process can comprise messages communicated through the portal, e.g., a web-browser application such that the pharmacist simply logs into the system and approves particular orders by mouse-clicks, keystrokes, and other conventional inputs that are forwarded to the local server that was the source of that particular dose order. A conventional login process with password and optionally further user-authentication ensures that the pharmacist's identity is verified before providing access to the pharmacist to any dose order information. The system can be designed so that for each dose order, the pharmacist must enter a unique identifier, such as a password, in order to release the drug. The date and time of the inspection and release or rejection of the dose order is also logged. Optionally, this information can be associated with the dose order record so that the approval stage is saved together with the processing steps to fill the dose order. In this manner, a record of which pharmacist has approved a particular dose order can be saved.

It will be appreciated that an entity can be formed in which pharmacist-members span the world in different time zones so as to have a pharmacist available regardless of the time of day to inspect and release or reject a particular dose order. The pharmacists can thus be part of an organization or a corporation that offers this service to different pharmacies across the globe. To accommodate different languages, the software can be configured to offer the dose order information in different languages, which can be selected in a pull down menu on a screen, such as a login screen.

With continued reference to FIG. 2, in step 230, if the pharmacist approves the dose order, then the dose order is released in step 240. The determination as to whether to approve the dose order is not managed by the present system. Rather, that determination is made by the pharmacist with the system providing detailed tracking of the recipe followed to prepare a particular dose order so that the pharmacist can make the approval decision using "over-the-shoulder" information, that is, information captured during the course of dose preparation as though he were looking over the shoulder of the operator of the workstation where the dose was prepared. On the other hand, if at step 230 the pharmacist does not approve the dose order based on the information presented to the pharmacist, then the dose order is rejected and the original order is added back the dose order queue at step 250 for preparation anew. At step 260, the local database and the situation board are updated to reflect whether the dose order was released or not. At a later time, the local database can communicate the completed dose information including any dose-approvals and dose-rejections from the local server 330 to the central server 390.

The above discussion is generally directed to the preparation and fulfillment of medication dose orders and the tracking of the dose order from origination to delivery. However, the present disclosure also applies to a method and system for the centralized preparation and delivery of medications in anticipation of use (i.e., at times before a patient-specific dose order has been prescribed or presented for fulfillment), such as described in the aforementioned U.S. application Ser. No. 11/844,135, by having workstation operators at manual workstations and automated workstations capture information at steps in the dose-order preparation process for approval as previously described.

With reference now to FIG. 3, topology 300 illustrates an environment in which a central server 390 communicates with local servers of each of potentially numerous pharmacies, hospitals, or other healthcare providers, each of which is generally identified at 310. These entities 310 can communicate with a respective local server 330 configured to implement the processes described herein (such as shown in FIGS. 1, 1A and 2) from a conventional pharmacy information system 320. The pharmacy information system 320 is the location where drug orders are initially entered for processing. The system 320 can thus include one or more stations where a doctor or other person can enter individual drug orders, such as orders for IV admixtures. The pharmacy information system 320 communicates with the local server 330 which preferably includes the functionality described above, including at least the label processing module that extracts drug order information from the pharmacy information system messages or data streams (and optionally a fulfillment module that determines whether new medication preparations are required or are already available in inventory), a database and a database query module that supports read and write operations to the database, and a communications module such as a web services module that supports communication with servers and other machines at remote locations. Optionally, the local server 330 comprises plural, dedicated servers. The pharmacy information system 320 and the local server 330 can be connected across various types of communication links or network segments. For example, communications can be transported over the Internet, a private network, or across a virtual private network (VPN). Further, the server 330 can communicate using a variety of communication interfaces such as IEEE 1284 (parallel port), USB or USB 2.0 port, IEEE 1394 ("Firewire"), IEEE 802.11 transceiver variants, Bluetooth transceiver, infrared port, or 10Base-T and 100Base-T Ethernet, or one of a variety of emerging interfaces. A variety of protocols can be employed for communication with the pharmacy information system 320 and with other workstation, databases, and servers and devices, including, for instance, TCP/IP and WAP. Communications between the entities 310 and the server 330 are preferably secure (e.g., utilize HTTPS, SSH, VPN, DES encryption or RSA encryption) so as to prevent the interception or snooping of potentially sensitive medical information such as patient history and medication orders.

Figure 4:
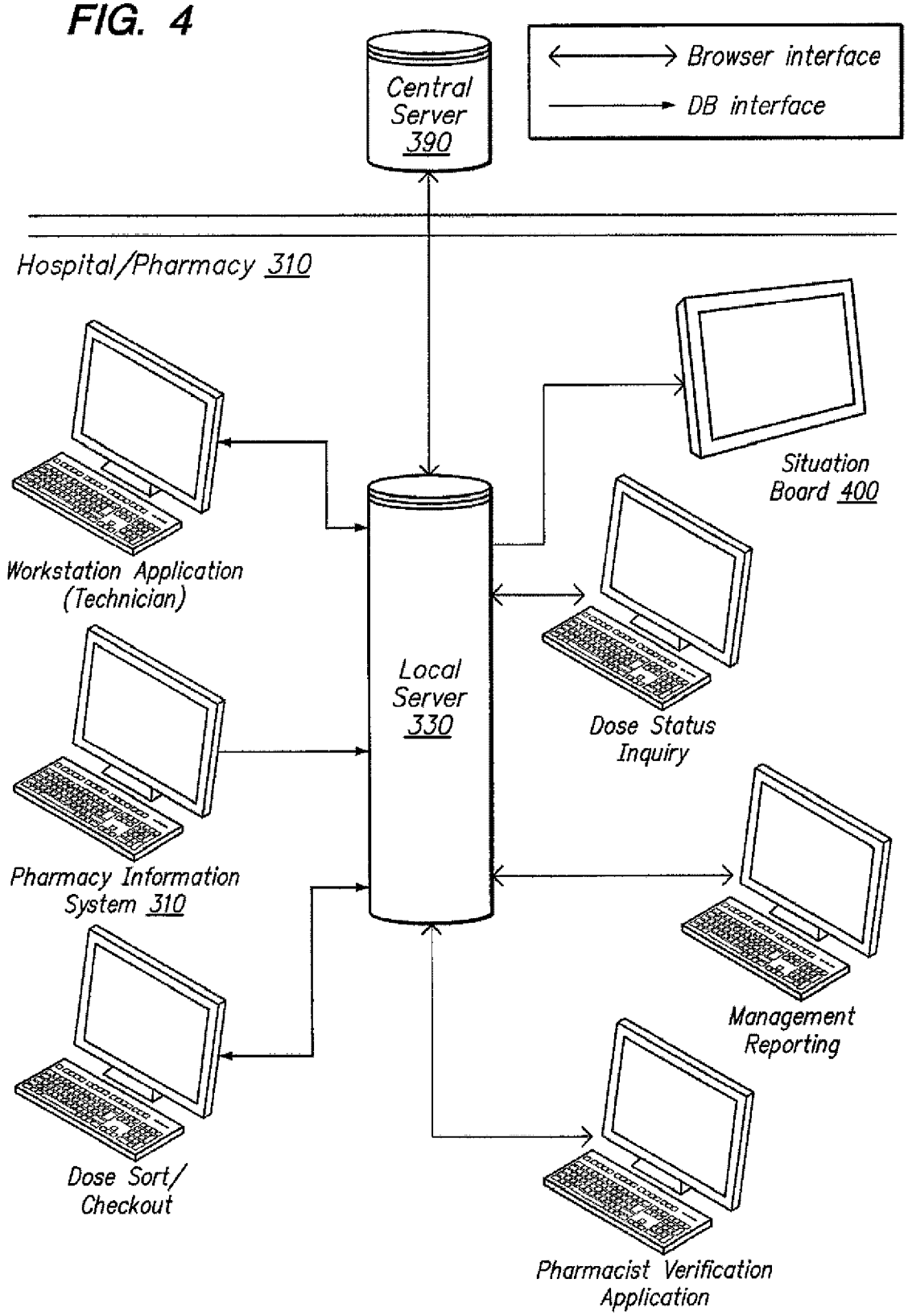
FIG. 4 illustrates a database and server arrangement for the preparation and management of medications in accordance with an embodiment of the present disclosure.

As illustrated in FIG. 4, the local server 330 within each hospital or pharmacy 310 is in communication with a number of devices and is in exclusive communication with the central server 390. The pharmacy information system provides label information to the database and that data is received at the local server 330 and processed by the label processing module as described above. Likewise, various workstations receive data from the local server and guide technicians in the preparation of medication doses while also providing captured images and other data to the database through communications with the local server. A pharmacist provides verification through a portal connection to the local server, such as a secure connection through the Internet, using a browser and/or an application that provides tools to aid in the review process (e.g., to magnify, rotate or otherwise manipulate the captured data associated with a given preparation). Finished doses are noted, sorted, and checked-out of the preparation queue or inventory as a function of the completion of process flows such as described above in connection with FIGS. 1, 1A, and 2. All the while, the situation board 400 presents metrics relating to the in-progress, yet-to-be-started, and completed doses using data provided by the local server, and more preferably from a dose status module operating on the local server or a machine connected thereto. Similarly, devices such as terminals can communicate with the local server 330 to query the status of dose preparation or gather reports on productivity, errors, workstation throughput, or other operational parameters (including parameters of interest to an information technology professional).

Beyond each of the pharmacies and hospitals that have a respective local server 330, there is a central server 390 that communicates only with the local servers. Each local server preferably runs a number of other services that assist in the management of information and periodic communication with the central server 390. In an implementation of the present disclosure, an Ensemble server includes a number of services in the form of code (e.g., software modules) that support system operation. For instance, a data backup and purge service has a rule base that defines the time period for the local server to maintain data. The time period is set so as to balance machine efficiency with the desirability of having data stored locally. This service operates to send data to the central server 390 at intervals or in response to events. Thus, for instance, data can be provided to the central server every minute and the local copy of any captured image data can be purged after 45 days. A system status service monitors the performance of the local server 330 and provides an administrator with information relating to the success or failure of data backup operations, system slowdowns, and the like. A dose order monitor service generates the data shown on the situation board 400, and the rules and parameters used for generating this data can be established in a profile that the service refers to. In addition, the dose order monitor service can advise of any doses that are not being made by any of the workstations at that particular location 310. A notification service operates to send messages such as emails by SMTP or instant messages using an IM protocol.

In one embodiment, the pharmacy information system 320 sends a label print stream to the server 330. The entity 310, whether it is a hospital, pharmacy, healthcare provider or the like communicates with the server 330 which, in turn, coordinates and manages the medication ordering and fulfillment process. Optionally, communication can be handled at the server 330 by a communication module. In addition, if the healthcare providers 310 communicate with the server 330 via a world-wide-web interface, the communications module can comprise a web server, such as Microsoft Internet Information Service (IIS) or Apache Web Server. The communications module, regardless of its form, preferably manages certain administrative and communication tasks so as to offload the processing demands placed on the server 330. For example, the communication module can authorize healthcare providers 310 access to data maintained by the server 330 through secure key or password protection. Further, the communications module can encrypt outgoing traffic and decrypt incoming traffic.

In the illustrated embodiment, the server 330 includes a label processing module and optionally an attached printer that can generate labels for medications prepared in anticipation of use as well as any medication doses that have been matched with a patient-specific dose order. Labels can be printed in standard fonts or typeface as well as be printed with bar-codes or otherwise encoded in a machine readable format. Furthermore, label printing can include electronically writing data to an RFID tag or similar device, if desired.

The label processing module can comprise code executing in the server so as to capture the printed label feeds, parse the labels, and post the dose order information into a database communicatively coupled to the server 330. The label processing module can be of the type described in commonly assigned U.S. Pat. No. 7,096,212, which is hereby incorporated by reference in its entirety. The label processing module supports a variety of methods for receiving label stream input including TCP, LPD, and any file transfer protocol. Preferably, the module includes language interpreters for a number of commonly used label-printer languages including Zebra, DataMax, SATO and Intermac.

Preferably, the server is able to receive and post to the database drug orders that are already in a format for posting, in other words, that do not require processing by the label processing module. Properly formatted drug orders can be posted using suitable database commands, such as commands in MySql, when a sequel database is used. Preferably, however, all drug orders from pharmacy information systems 310 pass through a processing module, even if not in the form of a "label" for data verification.

The server 330 also includes a local database (cache) server that is hosted locally at each site, such as a hospital or pharmacy, etc. The local database can be in the form of an Ensemble database, commercially available from InterSystems. The database stores a rolling "cache" of the current in-process work, as well as the works from a predefined number of previous days, such as the past 30-45 days, thereby creating a work order history that can be later accessed and reviewed even in if there is a temporary disruption of communication lines to a primary server at a different location. As described further below, the central server 390 preferably maintains an archive of data from each installation 310 and provides reporting functionality to thereby free the individual hospitals and pharmacies from maintaining all of the gathered data for an indefinite period of time. Data of various kinds including images (such as MEG images), are captured during the dose preparation process and this data is stored in the local Ensemble database. Thus, the incoming print stream that is received, parsed and interpreted by the label processing module can be placed into the local Ensemble database and that record augmented as the dose order is being filled with data collected during each or selected ones of the steps in the recipe for producing the drug in the drug order.

Unlike conventional messaging products, the Ensemble database has a high performance, highly scalable and SQL-compliant object database at its core. This database leverages technology found in a Cache product offered by InterSystems, and scales easily to handle thousands of simultaneous users and terabytes of data. All elements of Ensemble itself are modeled as object classes in its database. This object model is extended, during solution development, by Ensemble's advanced abstraction facility to all of the applications, services, data sources, business rules, and other components of an integrated solution.

Data is synchronized to a hosted central server 390, described below, via a network 301 (e.g., via SOAP web service process over HTTPS) and is eventually purged from the local server. The label processing module can run on the same physical machine as the local database (e.g., Ensemble local database). The central server 390 can securely manage data received from numerous entities 310, including entities that are not associated with one another.

The server 330 also includes management software, such as the Ensemble production module, that manages the status of doses through the system, and is configured to monitor and compute metrics that are to be displayed on the Situation Board 400. In addition, the Ensemble production module sends email notifications and manages communications with external systems, including the backup/synchronization process to the central server 390. The Ensemble production module runs on the local database.

The database and web server utilized by the server 330 should be provided locally by facilities at the entity 310.

The Situation Board 400 shown in FIG. 5 is a browser-based "dashboard" application that displays the overall status summary information about the current operations within the pharmacy IV room or another site. The Situation Board is displayed in the pharmacy on a large size, widescreen, flat panel display for high visibility and can include the following metrics: (1) count and percentage of doses awaiting preparation, in-process, or awaiting verification; (2) current productivity compared to a 30 day average (or some other average); (3) state of each workstation in all pharmacy locations in the hospital or the like; (4) wait time for preparation and verification for selected doses, such as STAT and "First Dose" orders.

The Situation Board 400 of FIG. 5 includes a number of different sections that present useful information to personnel. For example, the upper left hand corner includes a dose order summary 510 in the form of a bar graph that includes the types of doses (e.g., STAT, FIRST, WAIT, HAZMAT) along one axis and a percentage value along another axis. A color code is provided so that the operator can easily determine the percentage of each type of dose (as well as the total doses) that are pending, in-process and waiting for verification. In this example, 100% of the WAIT and HAZMAT type doses are pending. In a top center section, a dose order productivity reading 512 is presented to the operator and maps out the total count over a period of time and allows the operator to compare the current productivity reading compared to an average productivity reading. The bottom area of the screen (bottom left, center and right) 520 shows the wait time of various types of various doses. For example, the average wait time for the completion of the dose preparation is listed, as well as the average wait time for dose verification. Available workstations and the number of dose orders being handled by each workstation are identified by icons in the upper right corner of the screen.

The Situation Board 400 can be hosted on a machine running a conventional web browser application, including the server 330. To achieve ease of deployment and support for a broad base of client platforms, the majority of the present system can be presented through a web-browser interface. The main advantage of a web-based interface is to allow remote access from any location without the need to install any client applications on the end user's PC. Cache provides two avenues for developing web-based applications, namely, Cache Server Pages and Zen and additionally, ASP.NET can also be used to access data that resides in the local database 330. The Situation Board 400 is one example of the web-based interface of the present system and is a highly-visible dashboard application for obtaining at-a-glance status information about pending and in-process dose orders.

As previously mentioned, the server 330 and in particular, the local database thereof, periodically sends the set of completed work (and other data changes) back to the central server 390 for backup. Data transfers to the central server 390 can be quite frequent such as in response to each write operation to the database of the local server 330 or infrequent such as on the order of minutes or hours apart. A backup of all "log" data (i.e., completed doses, captured data including images, and action logs), as well as "static" data, such as formulary and procedure information, are stored on the central server 390. After a period of time has elapsed, such as 30 to 45 days, some of the data (e.g., captured images) or all of the data can be purged from the database of the local server 330 if the transfer to the central server 390 has been verified. Data can be segregated in the same database by customer ID (and other security "keys" as needed) to prevent customers from accessing any data but their own. This enables a central server to securely host a number of installations each having their own server 330. Moreover, multi-site hospital networks can also access data across a subset of customer IDs for all hospitals in their network, while maintaining those sites as separate and distinct entities.

A principal chore for the central server 390 is to manage the backup process that runs from each local site in response to their respective data uploads. Once the central server 390 has verified to the local server that it has received the dose order and dose preparation data records intact, the local server is then free to purge information in accordance with the data retention polices at that facility. Meanwhile, the central server 390 can retain all of the information in archive, or can maintain only dose related information such as which dose, what hospital, how many generated each day, who approved, and the like. Customers can also access the site periodically for query and reporting purposes. An ancillary benefit of having the central server 390 manage a plurality of entities 310 is that it is uniquely positioned to track actual dose dispensing in terms of which medications are dispensed and when within multiple geographic territories, providing a wealth of patient-independent information that can be mined, if desired.

In accordance with another aspect of the disclosure, the central server 390 can leverage the data-transfer relationship and support the data archiving functionality through a method of charging entities 310 on the basis of the number of doses prepared. Because each of the hospitals and pharmacies communicates regularly with the central server, and because the central server is maintaining information on prior dose-preparations, a tabulation module can operate to associate each data upload session with a particular installation and tally the number of records uploaded to the central server. At a prescribed interval, such as monthly or quarterly, an invoice can be generated in an amount that is a function of the quantity of information uploaded. Thus, the invoice can reflect a charge for each record uploaded, or a tiered-charge structure in which there is a fee for each of one or more bands of uploads (e.g., for the first 1000 uploads, the next 4000 uploads, etc.), or for the size of the upload (e.g., a charge calibrated to Gigabits of storage associated with that installation), as a few examples.

In yet a further aspect of the disclosure, the central server 390 can have a dose metrics module that processes incoming data from each particular hospital or pharmacy, and provides reports to administrators regarding the data from such hospital or pharmacy, or with respect to a group of hospitals or pharmacies that are commonly owned or that are in competing geographic, academic, or specialty areas. The dose metrics can be programmed to identify, among other parameters, how many different drugs a hospital, pharmacy or set of installations are using, the average time to produce a given dose, the number of errors in producing a given dose, the number of re-dos for a given dose.

As well, the dose metrics module can be programmed to benchmark the performance of a given hospital or pharmacy against that of another hospital or pharmacy. In this regard, a hospital system with multiple pharmacies can identify the most efficient or accurate pharmacies in its group, and can identify medication-preparation protocols that optimize processing through a comparative report across installations. Optimizations can be had at the operation level, as just described, and also with regard to resource allocation, such as by distributing drug orders that is statistically more likely to have fewer errors or faster handling of a given drug order (assuming there is more than one suitable pharmacy to select). Similarly, there can be new optimization capabilities at the purchasing level by comparing the handling of different drugs that are suitable for treating the same illness. For instance, if drugs A and B both are suitable for treating a given ailment, the drug metrics module might identify that drug A, although more costly, is more accurately prepared with fewer errors and re-dos and therefore is the better choice for filling the prescription, when substitutions are permitted. More generally, benchmarking includes an application of a rule base (algorithm) to the data collected from the various entities 310 to output a report or recommendation concerning future drug preparation, and that recommendation can concern training of pharmacists and their staff, workstation selection and quantity, hours of operation, material stocking, and the like.

The connection between the local server and the central server is over a network such as the Internet. The frequency of this backup can be hourly, daily, or at some other interval selected in view of the bandwidth available at the local site or other constraints or preferences. To provide additional safety, a secondary central site 392 can be provided and serve as an offsite disaster recovery site where critical data can be stored. The data can be sent (backed up) from the primary central server 390 to the secondary central site 392 in a conventional manner.

The server 330 is in bi-directional communication with a number of workstations to allow the workstations 500, 510, 520, etc., to receive the drug order queue and details concerning the individual drug orders. In addition, confirmatory acts that are performed at the workstations (e.g., capturing images and scanning barcodes) are transmitted to the server 330 for storing in the local database. Any number of different workstations can be a part of the present system. For example, FIG. 3 shows a FlowHood Workstation A 500; a FlowHood Workstation B 510 and a Chemo Workstation 520. However, other workstations can be part of the system including manual drug preparation workstations, automated workstations, and workstations that are specifically used to prepare a certain type of drug order can be connected to the server 330 to receive drug orders and report drug order processing.

A client application is provided at each workstation. The workstation can include a touch screen, one or more bar code scanners, label printers and a camera. Additional hardware that can be present at the workstation can include a scale, a reconstitution module (mixing station) and/or a security ID badge reader. The client application is preferably a web-based application and therefore, the specific location of the workstation relative to the server 330 is not critical since communication between the two is over a network, and so data and business logic of the server 330 can be communicated in a conventional manner, such as via a web-service using SSL http protocol (https) over the standard web port (80) that is typically available for web access through network firewalls. This architecture allows the server to be hosted locally, at the customer site, or at an ISP on the internet, with no changes to the application itself.

The drug order queue that is assembled in the server 330 is preferably displayed on the situation board 400 as well as at each of the various workstations. The display at the workstations can comprise a touch screen device to permit inputs via direct contact with the display. The touch screen can be provided at each location where doses are prepared, e.g., inside the pharmacy IV cleanroom. A camera is used to capture JPEG images or other images of dose preparation activities for later inspection (images are stored directly in the database). A foot-pedal, barcode scanner, and audible cues are used to keep the application hands-free during the preparation process. Unlike conventional systems where a single pharmacy printer prints all of the drug order labels prior to actually preparing the drug orders, the printing of the drug order labels preferably takes place only at the specific workstation that is fulfilling the drug order. Since the dose labels are printed at their point of use, the need to sort large batches of labels is eliminated, and therefore, they are prevented from getting lost in the pharmacy or being matched with the incorrect dose are minimized if not eliminated. Dose preparation instructions are presented to the technician as described herein. Detailed instructions and reference materials, such as PDF documents or web sites, can be referenced at the workstation.

The workstation communicates with the local database at the server 330 via a web service (e.g., SOAP web service) using the built-in web services capabilities of the server 330. Various reports can be generated via a connection to the database.

It will also be appreciated that the touch screen workstation can include voice recognition software to allow the operator to use voice commands to navigate. For example, the operator can navigate through a menu and review the drug order queue and even make a selection from the drug order queue using voice commands. By using the foot-pedal and voice commands, the operator can also capture images of the product and other objects as well as scanning the product, etc.

The work flow process described herein includes a "kitting" function that organizes work into appropriate kits, prints picking documents to assist the technician in locating and securing the appropriate drugs and supplies. Bar codes or the like can be used to verify the selected drugs and the work flow process includes issuing a kit report that tracks the work into and through the IV room or other room.

Dose tracking takes a number of forms. The situation board provides one manner of dose tracking because it maintains a high level view of the work being performed in the pharmacy and because is configured to immediately instruct an observer regarding any incomplete work. Moreover, color coding on the situation board can immediately identify the amount of work that is pending preparation, under preparation or prepared but not yet checked out by a pharmacist (i.e., orders not yet approved for release. Dose tracking is also provided at each step in the dose preparation process, including without limitation, the selection and preparation of the ingredients, pharmacist checking, removal from the IV room for delivery to a patient, and the actual delivery of the dose to the floor. Each of these steps is part of the work flow process that is tracked in the system managed by the server 330. As well, there is a dose query function that permits any authorized user to probe the database to discover the current status of any particular dose or group of doses. Also, the situation board maintains alarms for doses that are due and also tracks doses whose preparation must be delayed because of limited stability in solution.

Because the information is being stored in a database over long periods of time, the system develops metrics that demonstrate workload vs. staffing patterns; when the workload deviates from a "normal" condition, and when the workload is out of control; thereby permitting managers to adjust staffing for work load needs. Furthermore, the central server 390 can develop metrics that cover greater regions than gathered at any given server 330.

In yet another aspect of the present disclosure, the NDC number can be used when the system is configured to "push" the dose orders to the individual workstations. Incoming drug orders can be identified by their NDC numbers and the local server selects which workstation is best capable of handling the incoming dose order based, at least in part, by their NDC numbers and then assigns the dose order to the workstation. The dose order is then sent to the workstation for fulfillment of the order. For example, chemo drugs can be identified as such by their NDC number and the local server will select a workstation that is intended to handle chemodrugs. To implement this earmarked type routing, a database at the local server can include the NDC numbers to assist in routing certain medications to specific station or otherwise assist in ordering the drug orders on the situation board.

The present system therefore provides a composite workflow application that can layer on top of a hospital's existing pharmacy information system 320, without requiring any changes to that system, in order to manage the production of IV doses (and other doses) in the pharmacy, track dose delivery from the pharmacy, prevent medication errors caused by incorrect dose preparation, capture detailed history of dose preparation (including images), and serve as a gateway to automation systems throughout the pharmacy, such as carousels, compounders, and IV robots.

It will be appreciated that the present system eliminates the stacks of paper labels used by the current entirely manual process and the system provides greater visibility into the entire process, uses bar code verification to prevent the possibility of adverse drug events causes by dispensing errors, and improves the overall quality of life for the IV room or other department.

The present system combines a macro-level workflow manager that tracks the status of dose production in the pharmacy IV room from the receipt of the dose order, through preparation at a workstation that can include a laminar flow hood or chemotherapy bio-hazard cabinet, or distribution to an automated system for preparation, dose verification by a pharmacist, and finally to sorting and distribution from the pharmacy. Additionally, a micro-level workflow manager is provided at the dose preparation station. Using a combination of a touch screen, base code imager, camera, printer, foot pedal input and other equipment, the system ensures proper and complete preparation of each dose and provides full traceability to the products used during preparation.

In order to overcome the liabilities associated with a pure ASP mode, the workflow management system of the present disclosure is architected with a two-stage data process in which immediate operations are managed using a local server (also called a data cache) and such operations are continuously backed up to a network (Internet). The system therefore looks like an ASP to a user performing long term data retrieval and analysis, but on the other hand looks like a local application to the persons performing the mission-critical work. This ensures availability of critical data at all times for the entity 310 using the system.

The architecture is further divided into workstation applications that are deployed as thick clients to workstations located at each drug preparation area. The workstation applications are localized to the IV room and drive printers and other equipment, and so are more suitably deployed as thick clients. All other functions can be performed at any workstation at which the pharmacist finds him or herself, and so are mediated as thin clients using ubiquitous Internet browsers, which eliminates the need to physically deploy the software to those locations. This permits scalability and ready-access by a pharmacist that may be performing a drug dose inspection from a remote location.

In yet another aspect, the architecture and arrangement of the systems of the present disclosure provides the ability of multiple sites (local or remote) to place orders to a central filling site in a manner as described above. The central filling site processes each dose in accordance with the received instructions to generate a medication dose for delivery to a patient. As the medication dose is prepared, associated dose preparation data is generated at the central filling station and can be stored. The central filling site can then transfer the associated dose preparation data back to the ordering site using electronic means when the physical medication dose is sent back and received at the ordering site. Thus, the receipt of the medication dose along with the associated dose preparation data at the ordering site permits confirmation of the process, approval and release of the medication dose. For example, comparison between the dose preparation data and the medication dose (e.g., identifying information thereon (e.g., bar code, etc.) ensures the integrity of the dose preparation process. In addition, by having the dose preparation data, which can outline all the steps that were taken to prepare the dose, a person can more easily confirm and approve the dose preparation, thereby allowing the dose to be released to the patient. For example, as described above, each dose preparation can have a documented protocol (steps) that the person or machine follows to prepare the dose.

The present system provides a number of advantages including: (1) elimination of non-productive workload associated with label tracking and management; (2) elimination of non-productive time spent by pharmacists entering and leaving clean facilities used to prepare IVs for checking purposes; (3) provision of complete record-keeping on an activity that is now fundamentally impossible to document; (4) transfer of workload from scarce pharmacists to relatively abundant technicians; (5) entry of orders for IV admixtures into a hospital pharmacy information system that produces labels in a just-in-time manner for those doses that are actually being prepared and hence that are currently required for placement on the final drug dose; (6) transfer of label data to a server where they are electronically read and placed into a database; (7) configuration of computer workstations at each preparation location with knowledge of what doses on the list of pending doses their respective operators can prepare; (8) selection of doses by the user (typically, a pharmacy technician or operator) to be prepared, with labels printing only after that selection at a printer located at that workstation, with concomitant settings of that dose order as being "unavailable" to other workstations (this grouping of doses, all of which have the same medication(s) at the same dose(s), is called a "micro-batch").

While the example system has been described in connection with a certain embodiment thereof, the present system is not limited to the described embodiments but rather is more broadly defined by the recitations in the claims below and equivalents thereof.

The invention is claimed as follows:

1. A medication compounding workstation system comprising:
   a medication compounding workstation including:
      a communications interface configured to receive an electronic batch medication dose order for respective compounded medication doses over a network,
      a scanner configured to receive medication information scanned from at least one source medication container,
      an interactive graphical user interface configured to display, to a pharmacy operator, a set of steps for preparing the compounded medication doses, and
      a digital camera configured to capture digital images of the pharmacy operator preparing the compounded medication doses,
      wherein, for each step in the set of steps to prepare the compounded medication doses, the medication compounding workstation is configured to verify before moving to a next step that:
         (1) a source medication container suitable for preparing the compounded medication doses, as identified in medication information scanned from the source medication container, is present at the medication compounding workstation,
         wherein the medication compounding workstation is configured to display an error in real-time (i) requiring the pharmacy operator to repeat the respective step, and (ii) preventing the pharmacy operator from providing verification for a subsequent step if the medication compounding workstation does not receive verification that the source medication container suitable for preparing at least one of the compounded medication doses, as identified in the medication information scanned from the source medication container, is present at the medication compounding workstation, (2) if required by the step, that the digital image of the pharmacy operator preparing the compounded medication doses is captured and associatively stored with the electronic batch medication dose order in a database, and (3) if required by the step, that a user input from the pharmacy operator indicating completion of the step is captured and associatively stored with the electronic batch medication dose order in the database; and a portal that is accessible remotely from the medication compounding workstation and in communication with the database, the portal configured to at least one of:

display the associatively stored electronic batch medication dose order and the information used to verify completion of each step in the set of steps to prepare the compounded medication doses for subsequent inspection or approval of the completed electronic batch medication dose order, and display reports relating to the preparation of the compounded medication doses.

2. The system of claim 1, wherein the medication compounding workstation is configured to cause a label to be printed, the label identifying a completed electronic batch medication dose order.

3. The system of claim 1, wherein the interactive graphical user interface is configured to receive a user input requesting additional information related to the electronic batch medication dose order and a selected step in the set of steps to prepare the compounded medication doses.

4. The system of claim 1, wherein the medication information is scanned using a barcode scanner.

5. The system of claim 1, wherein the medication compounding workstation is configured to display, in the interactive graphical user interface, each step in the set of steps based on a sequence specified by a protocol that must be undertaken to prepare the compounded medication doses.

6. The system of claim 5, wherein the protocol is electronically stored with a plurality of different protocols, and wherein the medication compounding workstation is configured to determine the electronic batch medication dose order is associated with the protocol before retrieving the protocol.

7. The system of claim 6, wherein the medication compounding workstation is configured to determine the association between the electronic batch medication dose order and the protocol based on a match between at least one of a medication and a form of dose specified within each of the electronic batch medication dose order and the protocol.

8. The system of claim 6, wherein the input related to the preparation of the compounded medication doses includes a measurement performed by at least one of a scale, a hydrometer, and a spectrometer on at least one of the completed compounded medication doses corresponding to the electronic batch medication dose order, medication in the at least one source medication container, and an intermediary mixture formed during the step, and wherein completion for each step in the set of steps is alternatively based on receipt of the measurement within an acceptable range.

9. The system of claim 8, wherein the medication compounding workstation is configured to prevent the pharmacy operator from completing the protocol if the measurement is outside the acceptable range.

10. The system of claim 8, wherein the measurement is received electronically in the medication compounding workstation from the at least one of the scale, the hydrometer, and the spectrometer.

11. The system of claim 1, wherein the medication compounding workstation is configured to display, in the interactive graphical user interface, a completion progress indication for each step in the set of steps after verification of the completion of the respective step.

12. The system of claim 1, wherein the medication compounding workstation is configured to:

determine one step in the set of steps to prepare the compounded medication doses has not been verified as being complete;

flag the electronic batch medication dose order as being incomplete due to an error; and associatively store in the database the electronic batch medication dose order, the flag, and the determined one step that has not been verified as being complete.

13. The system of claim 12, wherein the medication compounding workstation is configured to permit processing of another electronic batch medication dose order after the electronic batch medication dose order has been flagged as being incomplete.

14. The system of claim 1, wherein the medication compounding workstation is configured to store the electronic batch medication dose order to a queue after receiving the electronic batch medication dose order over the network.

15. The system of claim 1, wherein the digital image includes at least one of the at least one source medication container including an identification of a medication name, a lot number, an expiration date, and quality control information.

16. The system of claim 1, wherein the portal is configured to transmit to the medication compounding workstation a message indicative that the compounded medication doses can be released if the information used to verify completion of each step in the set of steps to prepare the compounded medication doses is approved.

17. The system of claim 16, wherein the medication compounding workstation is configured to display release information indicative that the compounded medication doses can be released after receiving the message from the portal.

18. The system of claim 1, wherein the medication compounding workstation is configured to:

receive an identity of the pharmacy operator; and associate the identity of the pharmacy operator with the digital images of the pharmacy operator preparing the compounded medication doses.

19. The system of claim 18, wherein the medication compounding workstation is configured to receive the identity of the pharmacy operator from at least one of a fingerprint reader, a key-card reader, and the interactive graphical user interface.

20. The system of claim 18, wherein the medication compounding workstation is configured to use the identity of the pharmacy operator to verify before moving to a next step that the pharmacy operator is authorized to perform the step.

* * * * *